United States Patent [19]
Shoji et al.

[11] Patent Number: 5,707,997
[45] Date of Patent: Jan. 13, 1998

[54] PYRAZOLO[1,5-A]PYRIMIDINE DERIVATIVE

[75] Inventors: Yasuo Shoji; Makoto Inoue; Takashi Okamura; Kinji Hashimoto, all of Naruto; Masayuki Ohara, Itano-gun; Tsuneo Yasuda, Naruto, all of Japan

[73] Assignee: Otsuka Pharmaceutical Factory, Inc., Tokushima, Japan

[21] Appl. No.: 602,824

[22] PCT Filed: Jun. 5, 1995

[86] PCT No.: PCT/JP95/01104
§ 371 Date: Feb. 21, 1996
§ 102(e) Date: Feb. 21, 1996

[87] PCT Pub. No.: WO95/35298
PCT Pub. Date: Dec. 28, 1995

[30] Foreign Application Priority Data

Jun. 21, 1994 [JP] Japan .................................. 6-138635
Mar. 14, 1995 [JP] Japan .................................. 7-53997

[51] Int. Cl.$^6$ ........................ A61K 31/505; C07D 403/02
[52] U.S. Cl. ........................................... 514/258; 544/281
[58] Field of Search ............................... 544/281; 514/258

[56] References Cited

U.S. PATENT DOCUMENTS 3,925,385 12/1975 O'Brien et al. ....................... 260/256.4
4,950,585 8/1990 Tachibana et al. ...................... 430/385
5,478,838 12/1995 Arita et al. ............................ 514/300
5,571,813 11/1996 Rühter et al. .......................... 514/257

FOREIGN PATENT DOCUMENTS 0 591 528  4/1994  European Pat. Off. .

OTHER PUBLICATIONS

Derwent Abstract of JP-B1-43-25504, Aug. 1984.
Derwent Abstract of JP-A1-61-57587, Mar. 1964.
Derwent Abstract of JP-B1-42-3171, Nov. 1968.
Journal of Medicinal Chemistry, vol. 20, No. 2, Feb. 1977.
Journal of Heterocyclic Chemistry, vol. 22, No. 3, May–Jun. 1985.

*Primary Examiner*—Matthew V. Grumbling
*Attorney, Agent, or Firm*—Sughrue, Mion, Zinn, Macpeak & Seas, PLLC

[57] ABSTRACT

The invention provides a pyrazolo[1,5-a]pyrimidine derivative of the following formula (1):

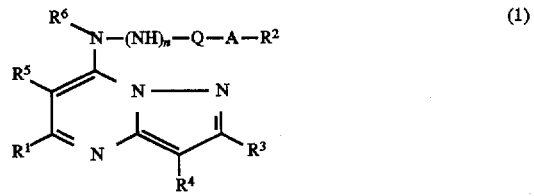

wherein $R^1$, $R^3$, $R^4$, $R^5$, $R^6$, Q, A and n are defined in the description; and $R^2$ is naphthyl, cycloalkyl, furyl, thienyl, optionally halogen-substituted pyridyl, optionally halogen-substituted phenoxy, or phenyl which may have 1 to 3 substituents selected from the group consisting of lower alkyl, lower alkoxy, halogen, nitro, halogen-substituted lower alkyl, halogen-substituted lower alkoxy, lower alkoxycarbonyl, hydroxyl, phenyl(lower)alkoxy, amino, cyano, lower alkanoyloxy, phenyl and di(lower)alkoxyphosphoryl(lower)alkyl. This derivative is useful as a potent analgesic.

10 Claims, No Drawings

PYRAZOLO[1,5-A]PYRIMIDINE DERIVATIVE

This is a national stage application, filed under 35 USC 371, of PCT/JP95/01104, filed Jun. 5, 1995.

TECHNICAL FIELD

The present invention relates to novel pyrazolo[1,5-a]pyrimidine derivatives.

PRIOR ART

The pyrazolo[1,5-a]pyrimidine derivatives of the invention are novel compounds which have never been published in the literature.

DISCLOSURE OF THE INVENTION

The object of the invention is to provide compounds of value as medicines as will be described hereinafter.

The present invention provides a novel pyrazolo[1,5-a]pyrimidine derivative of the following formula (1):

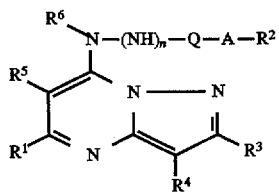

(1)

wherein $R^1$ is hydrogen, lower alkyl which may have thienyl, lower alkoxy, lower alkylthio, oxo or hydroxyl as a substituent, cycloalkyl, thienyl, furyl, lower alkenyl, or phenyl which may have 1 to 3 substituents selected from the group consisting of lower alkyl, lower alkoxy, phenylthio and halogen; $R^2$ is naphthyl, cycloalkyl, furyl, thienyl, optionally halogen-substituted pyridyl, optionally halogen-substituted phenoxy, or phenyl which may have 1 to 3 substituents selected from the group consisting of lower alkyl, lower alkoxy, halogen, nitro, halogen-substituted lower alkyl, halogen-substituted lower alkoxy, lower alkoxycarbonyl, hydroxyl, phenyl(lower)alkoxy, amino, cyano, lower alkanoyloxy, phenyl and di(lower)alkoxyphosphoryl(lower)alkyl; $R^3$ is hydrogen, phenyl or lower alkyl; $R^4$ is hydrogen, lower alkyl, lower alkoxycarbonyl, phenyl(lower)alkyl, optionally phenylthio-substituted phenyl, or halogen; $R^5$ is hydrogen or lower alkyl; $R^6$ is hydrogen, lower alkyl, phenyl(lower)alkyl, or benzoyl having 1 to 3 substituents selected from the group consisting of lower alkoxy, halogen-substituted lower alkyl and halogen; $R^1$ and $R^5$ may conjointly form lower alkylene; Q is carbonyl or sulfonyl; A is a single bond, lower alkylene or lower alkenylene; and n is 0 or 1.

Examples of the groups in the above formula (1) are as follows. The lower alkyl group includes straight- or branched-chain lower alkyl groups such as methyl, ethyl, propyl, isopropyl, butyl, isobutyl, tert-butyl, pentyl, hexyl, and the like.

The cycloalkyl group includes cyclopropyl, cyclobutyl, cyclopentyl, cyclohexyl, cycloheptyl, cyclooctyl, and the like.

The lower alkoxy group includes methoxy, ethoxy, propoxy, isopropoxy, butoxy, pentyloxy, hexyloxy, and the like.

The lower alkylthio group includes methylthio, ethylthio, propylthio, butylthio, pentylthio, hexylthio, and the like.

The halogen atom includes fluorine, chlorine, bromine and iodine.

The halogen-substituted lower alkyl group includes trifluoromethyl, pentafluoroethyl, heptafluoropropyl, nonafluorobutyl, undecafluoropentyl, tridecafluorohexyl, and the like.

The halogen-substituted lower alkoxy group includes trifluoromethoxy, pentafluoroethoxy, heptafluoropropoxy, nonafluorobutoxy, undecafluoropentyloxy, tridecafluorohexyloxy, and the like.

The lower alkoxycarbonyl group includes methoxycarbonyl, ethoxycarbonyl, propoxycarbonyl, isopropoxycarbonyl, butoxycarbonyl, pentyloxycarbonyl, hexyloxycarbonyl, and the like.

The di(lower)alkoxyphosphoryl(lower)alkyl group includes dimethoxyphosphorylmethyl, diethoxyphosphorylmethyl, dipropoxyphosphorylmethyl, diisopropoxyphosphorylmethyl, dibutoxyphosphorylmethyl, dipentyloxyphosphorylmethyl, dihexyloxyphosphorylmethyl, 2-(dimethoxyphosphoryl)ethyl, 2-(diethoxyphosphoryl)ethyl, 3(diethoxyphosphoryl)propyl, and the like.

The naphthyl group includes 1-naphthyl, 2-naphthyl, and the like.

The lower alkylene group includes methylene, ethylene, trimethylene, tetramethylene, pentamethylene, hexamethylene, and the like.

The lower alkenylene group includes vinylene, propenylene, and the like.

The optionally halogen-substituted pyridyl group includes 2-pyridyl, 3-pyridyl, 4-pyridyl, 6-chloro-2-pyridyl, 5-chloro-2-pyridyl, 4-chloro-2-pyridyl, 3-chloro-2-pyridyl, 6-chloro-3-pyridyl, 5-chloro-3-pyridyl, 4-chloro-3-pyridyl, 2-chloro-3-pyridyl, 2-chloro-4-pyridyl, 3-chloro-4-pyridyl, 6-fluoro-3-pyridyl, 6-bromo-3-pyridyl, 6-iodo-3-pyridyl, and the like.

The optionally halogen-substituted phenoxy group includes phenoxy, 2-chlorophenoxy, 3-chlorophenoxy, 4-chlorophenoxy, 4-fluorophenoxy, 4-bromophenoxy, 4-iodophenoxy, and the like.

The thienyl group includes 2-thienyl and 3-thienyl, and the furyl group includes 2-furyl and 3-furyl.

The lower alkenyl group includes vinyl, allyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, and the like.

The phenyl(lower)alkyl group includes benzyl, 1-phenylethyl, 2-phenylethyl, 3-phenylpropyl, 4-phenylbutyl, 5-phenylpentyl, 6-phenylhexyl, and the like.

The phenyl(lower)alkoxy group includes benzyloxy, 2-phenylethoxy, 3-phenylpropoxy, 4-phenylbutoxy, 5-phenylpentyloxy, 6-phenylhexyloxy, and the like.

The lower alkanoyloxy group includes acetoxy, propionyloxy, butyryloxy, valeryloxy, pivaloyloxy, hexanoyloxy, heptanoyloxy, and the like.

The lower alkyl group which may have thienyl, lower alkoxy, lower alkylthio, oxo or hydroxyl as a substituent includes not only the above-mentioned non-substituted lower alkyl groups but also 2-thienylmethyl, 3-thienylmethyl, 1-(2-thienyl)ethyl, 1-(3-thienyl)ethyl, 2-(2-thienyl)ethyl, 2-(3-thienyl)ethyl, 3-(2-thienyl)propyl, 4-(2-thienyl)butyl, 5-(2-thienyl)pentyl, 6-(2-thienyl)hexyl, methoxymethyl, ethoxymethyl, propoxymethyl, butoxymethyl, pentyloxymethyl, hexyloxymethyl, 1-methoxyethyl, 2-methoxyethyl, 3-methoxypropyl, 4-methoxybutyl, 5-methoxypentyl, 6-methoxyhexyl, hydroxymethyl, 1-hydroxyethyl, 2-hydroxyethyl, 1-hydroxypropyl, 2-hydroxypropyl, 3-hydroxypropyl, 3-hydroxybutyl, 4-hydroxypentyl, 5-hydroxyhexyl, methylthiomethyl, ethylthiomethyl, propylthiomethyl, butylthiomethyl, pentylthiomethyl, hexylthiomethyl, 2-methylthioethyl, 3-methylthiopropyl, 4-methylthiobutyl, 5-methylthiopentyl, 6-methylthiohexyl, formyl, formylmethyl, acetyl, 2-formylethyl, 2-oxopropyl, propionyl, 3-formylpropyl, 3-oxobutyl, 2-oxobutyl, butyryl, 4-formylbutyl, 4-oxopentyl, 3-oxopentyl, 2-oxopentyl, valeryl, 5-formylpentyl, 5-oxohexyl, 4-oxohexyl, 3-oxohexyl, 2-oxohexyl, hexanoyl, and the like.

The phenyl group which may have 1 to 3 substituents selected from the group consisting of lower alkyl, lower alkoxy, phenylthio and halogen includes phenyl, 2-methylphenyl, 3-methylphenyl, 4-methylphenyl, 4-ethylphenyl, 4-propylphenyl, 4-butylphenyl, 4-t-butylphenyl, 4-pentylphenyl, 4-hexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methoxyphenyl, 3-methoxyphenyl, 4-methoxyphenyl, 4-ethoxyphenyl, 4-propoxyphenyl, 4-butoxyphenyl, 4-pentyloxyphenyl, 4-hexyloxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,4,5-trimethoxyphenyl, 2-chlorophenyl, 3-chlorophenyl, 4-chlorophenyl, 4-bromophenyl, 4-iodophenyl, 4-fluorophenyl, 4-(phenylthio)phenyl, 3-(phenylthio)phenyl, 2-(phenylthio)phenyl, and the like.

The phenyl group which may have 1 to 3 substituents selected from the group consisting of lower alkyl, lower alkoxy, halogen, nitro, halogen-substituted lower alkyl, halogen-substituted lower alkoxy, lower alkoxycarbonyl, hydroxyl, phenyl(lower)alkoxy, amino, cyano, lower alkanoyloxy, phenyl and di(lower)alkoxyphosphoryl-(lower)alkyl include the following groups:

phenyl, 2-methylphenyl, 3-methylphenyl, 4-methylphenyl, 4-ethylphenyl, 4-propylphenyl, 4-butylphenyl, 4-t-butylphenyl, 4-pentylphenyl, 4-hexylphenyl, 2-methoxyphenyl, 3-methoxyphenyl, 4-methoxyphenyl, 4-ethoxyphenyl, 4-propoxyphenyl, 4-butoxyphenyl, 4-pentyloxyphenyl, 4-hexyloxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxyphenyl, 3,4,5-trimethoxyphenyl, 3,4,5-triethoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2,3-dichlorophenyl, 2,4-dichlorophenyl, 2-nitrophenyl, 3-nitrophenyl, 4-nitrophenyl, 2-trifluoromethylphenyl, 3-trifluoromethylphenyl, 4-trifluoromethylphenyl, 4-pentafluoroethylphenyl, 4-heptafluoropropylphenyl, 4-nonafluorobutylphenyl, 4-undecafluoropentylphenyl, 4-tridecafluorohexylphenyl, 2-methoxycarbonylphenyl, 3-methoxycarbonylphenyl, 4-methoxycarbonylphenyl, 4-ethoxycarbonylphenyl, 4-propoxycarbonylphenyl, 4-butoxycarbonylphenyl, 4-pentyloxycarbonylphenyl, 4-hexyloxycarbonylphenyl, 2-biphenyl, 3-biphenyl, 4-biphenyl, 2-(diethoxyphosphorylmethyl)phenyl, 3-(diethoxyphosphorylmethyl)phenyl, 4-(diethoxyphosphoryl-methyl)phenyl, 4-(dimethoxyphosphorylmethyl)phenyl, 4-(diisopropoxyphosphorylmethyl)phenyl, 3,5-dimethoxy-4-ethoxyphenyl, 3,5-dimethoxy-4-propoxyphenyl, 4-butoxy-3,5-dimethoxyphenyl, 3,5-dimethoxy-4-pentyloxyphenyl, 3,5-dimethoxy-4-hexyloxyphenyl, 2,3-bis (trifluoro-methyl)phenyl, 2,4-bis(trifluoromethyl)phenyl, 2,5-bis(trifluoromethyl)phenyl, 2,6-bis(trifluoromethyl) phenyl, 3,4-bis(trifluoromethyl)phenyl, 3,5-bis (trifluoromethyl)phenyl, 3,5-dimethoxy-4-hydroxyphenyl, 3,5-diethoxy-4-hydroxyphenyl, 3,5-dipropoxy-4-hydroxyphenyl, 4-benzyloxy-3,5-dimethoxyphenyl, 4-benzyloxy-3,5-diethoxyphenyl, 3,5-dimethoxy-4-(2-phenylethoxy)phenyl, 4-acetoxy-3,5-dimethoxyphenyl, 3,5-dimethoxy-4-propionyloxyphenyl, 2-chloro-3,5-dimethoxyphenyl, 4-chloro-3,5-dimethoxyphenyl, 4-bromo-3,5-dimethoxyphenyl, 3,5-dimethoxy-4-iodophenyl, 3,5-dichloro-4-methoxyphenyl, 3,5-dichloro-4-5 ethoxyphenyl, 2-aminophenyl, 3-aminophenyl, 4-aminophenyl, 2-cyanophenyl, 3-cyanophenyl, 4-cyanophenyl, 4-trifluoromethoxyphenyl, 3-trifluoromethoxyphenyl, 2-trifluoromethoxyphenyl, 4-pentafluoroethoxyphenyl, 4-heptafluoropropoxyphenyl, 4-nonafluorobutoxyphenyl, 4-undecafluoropentyloxyphenyl, 4-tridecafluorohexyloxyphenyl, 3,5-bis(trifluoromethoxy)phenyl, 3,4,5-tris (trifluoromethoxy)phenyl, and the like.

The optionally phenylthio-substituted phenyl group includes phenyl, 4-(phenylthio)phenyl, 3-(phenylthio) phenyl, 2-(phenylthio)phenyl, and the like.

The benzoyl group having 1 to 3 substituents selected from the group consisting of lower alkoxy, halogen-substituted lower alkyl and halogen include 2-chlorobenzoyl, 3-chlorobenzoyl, 4-chlorobenzoyl, 2-fluorobenzoyl, 2-bromobenzoyl, 2-iodobenzoyl, 2,4-dichlorobenzoyl, 3,4-dichlorobenzoyl, 2,5-dichlorobenzoyl, 2,6-dichlorobenzoyl, 2-trifluoromethylbenzoyl, 3-trifluoromethylbenzoyl, 4-trifluoromethylbenzoyl, 3,5-bis (trifluoromethyl)benzoyl, 3,4,5-tris(trifluoromethyl) benzoyl, 2-methoxybenzoyl, 3-methoxybenzoyl, 4-methoxybenzoyl, 2,3-dimethoxybenzoyl, 2,4-dimethoxybenzoyl, 3,5-dimethoxybenzoyl, 3,4,5-trimethoxybenzoyl, 2-ethoxybenzoyl, 2-propoxybenzoyl, 2-butoxybenzoyl, 2-pentyloxybenzoyl, 2-hexyloxybenzoyl, and the like.

The pyrazolo[1,5-a]pyrimidine derivatives of formula (1) according to the invention have potent analgesic effects and are useful as analgesics to relieve pains such as postoperative pain, migraine, gout, cancer pain, chronic pain and neuropathic pain. Furthermore, the derivatives of the invention are free of side effects typical of conventional analgesics, do not cause hallucination or derangement and are not addictive.

Examples of preferred pyrazolo[1,5-a]pyrimidine derivatives of the invention for use as the analgesics are: compounds of formula (1) wherein Q is carbonyl and n is 0; compounds wherein Q is carbonyl, n is 1, $R^1$ is lower alkyl or phenyl, $R^2$ is phenyl having 1 to 3 substituents selected from the group consisting of lower alkoxy and halogen-substituted lower alkyl, $R^3$, $R^4$, $R^5$ and $R^6$ are each hydrogen, and A is a single bond; and compounds wherein Q is sulfonyl, n is 0, $R^1$ is lower alkyl, $R^2$ is phenyl which may have 1 to 3 halogens, $R^3$, $R^4$, $R^5$ and $R^6$ are each hydrogen, and A is a single bond.

Of these preferred pyrazolo[1,5-a]pyrimidine derivatives, the following compounds are more preferable.

(1) Compounds wherein $R^1$ is optionally lower alkylthio-substituted lower alkyl or optionally phenylthio-substituted phenyl, $R^2$ is phenyl having 1 to 3 substituents selected from the group consisting of lower alkoxy, halogen and halogen-substituted lower alkyl, $R^3$ is hydrogen or phenyl, $R^4$ is hydrogen, halogen or phenyl, $R^5$ is hydrogen, $R^6$ is hydrogen or benzoyl having halogen-substituted lower alkyl as a substituent, Q is carbonyl and A is a single bond;

(2) compounds wherein $R^3$, $R^4$ and $R^6$ are each hydrogen, n is 0, $R^1$ is n-butyl and $R^2$ is phenyl having either 2 to 3 lower alkoxy groups or 1 to 2 halogen-substituted lower alkyl groups, or $R^1$ is phenyl and $R^2$ is phenyl having 3 lower alkoxy groups; and (3) compounds wherein $R^2$ is 2,4-dimethoxyphenyl, 3,4,5-trimethoxyphenyl, 2-trifluoromethylphenyl or 2,5-bis(trifluoromethyl)phenyl.

Examples of most preferred pyrazolo[1,5-a]pyrimidine derivatives of the invention are 5-n-butyl-7-(3,4,5-trimethoxybenzoylamino)pyrazolo[1,5-a]pyrimidine and 5-n-butyl-7-(2-trifluoromethylbenzoylamino)pyrazolo[1,5-a]pyrimidine.

The derivatives of formula (1) according to the invention can be produced by various processes. Some exemplary processes are schematically shown hereinafter.

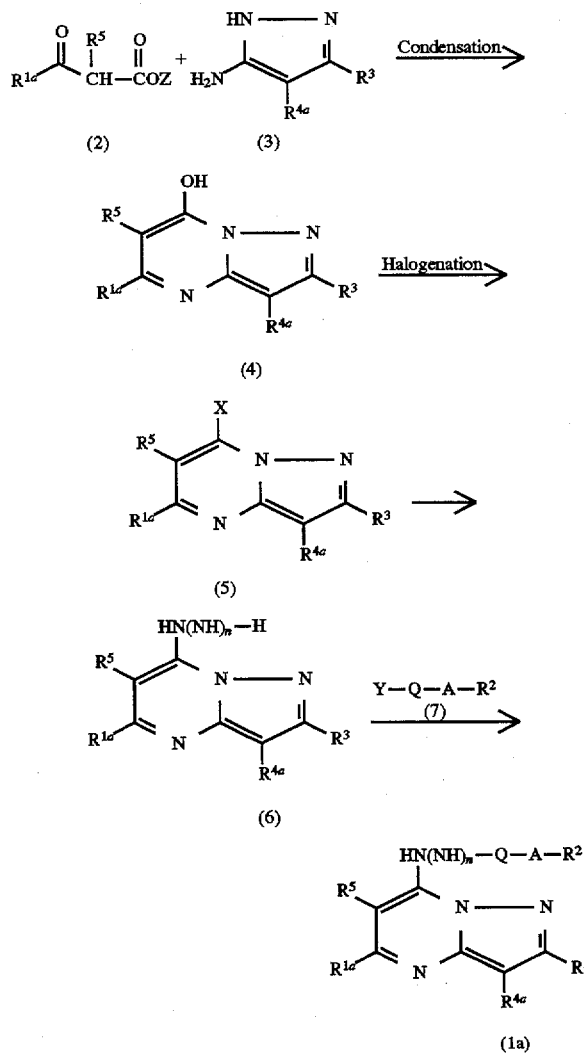

wherein $R^2$, $R^3$, $R^5$, n, Q and A are as defined above, $R^{1a}$ is hydrogen, lower alkyl which may have thienyl, lower alkoxy or lower alkylthio as a substituent, cycloalkyl, thienyl, furyl, lower alkenyl, or phenyl which may have 1 to 3 substituents selected from the group consisting of lower alkyl, lower alkoxy, phenylthio and halogen, $R^{1a}$ and $R^5$ may conjointly form lower alkylene, $R^{4a}$ is hydrogen, lower alkyl, lower alkoxycarbonyl, phenyl(lower)alkyl, or optionally phenylthio-substituted phenyl, X and Y are each halogen, and Z is lower alkyl.

The condensation of the compounds (2) and (3) in Reaction Scheme-1 is carried out in a suitable inert solvent at room temperature to the boiling point of the solvent. Examples of useful inert solvents are acetic acid, ethanol, benzene, toluene, xylene and tetrahydrofuran (THF). The compounds (2) and (3) are preferably used in an approximately equimolar proportion. The reaction is carried out for about 2-5 hours to provide the desired compound (4).

The subsequent halogenation of the compound (4) is carried out using a halogenating agent such as phosphorus oxychloride and phosphorus oxybromide in the presence of a suitable acid acceptor such as N,N-dimethylaniline, N,N-diethylaniline and triethylamine. Since the said halogenating agents also function as solvents, there is no need to use other solvents in this reaction but an inert solvent such as benzene, toluene and xylene may be optionally used. The acid acceptor is preferably used in an amount of about 1-10 equivalents relative to the compound (4). The reaction is carried out at approximately room temperature to 150° C. for about 0.5-12 hours.

The halide (5) obtained by this reaction is treated with aqueous ammonia or hydrazine to convert the halide into the compound (6). This treatment requires no solvents and is generally carried out by heating the compound (5) with an excess of aqueous ammonia at about 100°-150° C. for about 1-12 hours or treating the compound (5) with an excess of hydrazine at about 0° C. to room temperature for about 5-30 hours.

The compound (6) thus obtained is reacted with acid halide (7) to convert the compound (6) into the compound (1) of the invention. This reaction can be carried out in a suitable solvent in the presence of an acid acceptor. Examples of useful solvents are aromatic or aliphatic hydrocarbons such as benzene, toluene, xylene and petroleum ether; chain or cyclic ethers such as diethylether, dimethoxyethane, tetrahydrofuran (THF) and 1,4-dioxane; ketones such as acetone, ethylmethylketone and acetophenone; hydrocarbon halides such as dichloromethane, chloroform, carbon tetrachloride and 1,2-dichloroethane. Examples of useful acid acceptors are tertiary amines such as triethylamine, N,N-diethylaniline, N-methylmorpholine, pyridine and 4-methylaminopyridine.

There is no specific limitation on the amounts of the acid halide (7) and the acid acceptor relative to the compound (6) in this reaction. It is, however, preferable that the acid halide be used in an approximately equimolar proportion and the acid acceptor in an approximately equimolar to excessive amount. The reaction goes to completion at room temperature to reflux temperature of the solvent in about 0.5-20 hours.

Compound (6'), i.e., the compound (6) wherein n=0 can be produced by the process shown in Reaction Scheme-1'.

[Reaction Scheme-1']

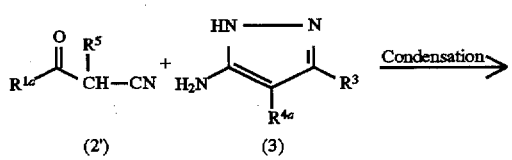

-continued
[Reaction Scheme-1']

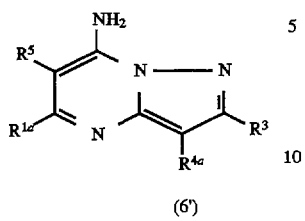

(6')

wherein $R^{1a}$, $R^3$, $R^{4a}$ and $R^5$ are as defined above

The condensation of the nitrile derivative (2') and the compound (3) in this scheme is carried out in an inert solvent such as benzene, toluene, xylene, acetic acid and ethanol at room temperature to reflux temperature of the solvent for about 2–10 hours. These two compounds are generally used in an approximately equimolar proportion.

[Reaction Scheme-2]

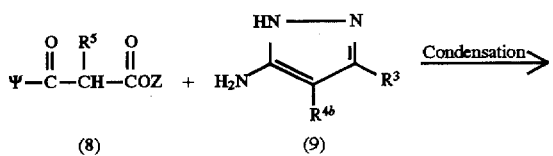

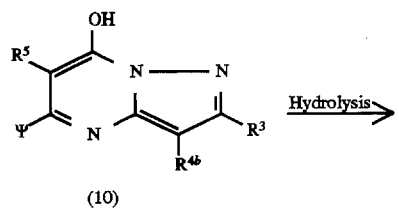

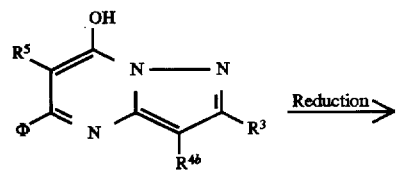

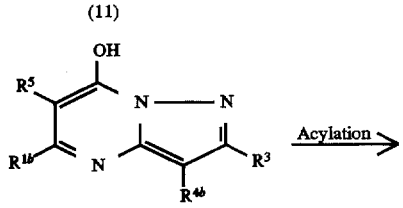

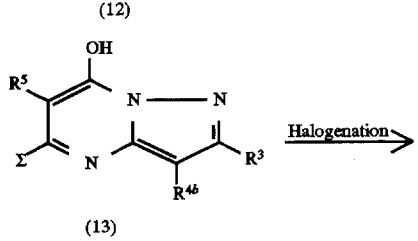

-continued
[Reaction Scheme-2]

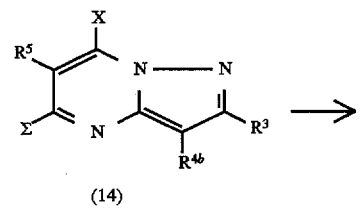

(14)

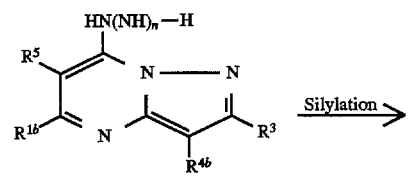

(15)

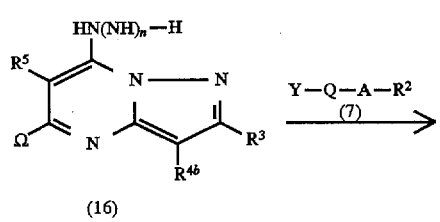

(16)

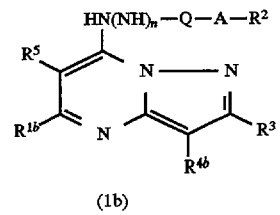

(1b)

wherein $R^2$, $R^3$, $R^5$, X, Y, A, Q, Z and n are as defined above, $\Psi$ is lower alkyl having protected oxo, $\Phi$ is lower alkyl having oxo, $\Sigma$ is lower alkyl having acyloxy, $\Omega$ is lower alkyl having tri(lower)alkyl-silyloxy, $R^{1b}$ is hydroxy(lower)alkyl, $R^{4b}$ is hydrogen, lower alkyl, phenyl(lower)alkyl or optionally phenylthio-substituted phenyl.

The condensation of the compounds (8) and (9) in Reaction Scheme-2 can be carried out in the same manner as the condensation of the compounds (2) and (3) in Reaction Scheme-1.

Examples of the lower alkyl having protected oxo and represented by $\Psi$ in the compound (8) include lower alkyl groups having as protected oxo the residue of di(lower)alkyl acetal such as dimethylacetal, methylethylacetal, diethylacetal, dipropylacetal, dibutylacetal, dipentylacetal and dihexylacetal or the residue of cyclic acetal such as ethylene acetal, trimethylene acetal and tetramethylene acetal.

The subsequent hydrolysis of the compound (10) according to Reaction Scheme-2 can be carried out using an organic acid such as acetic acid, propionic acid and p-toluenesulfonic acid. Of these organic acids, carboxylic acids such as acetic acid and propionic acid function as solvents. When such a carboxylic acid is used, no other solvents are necessary. Other suitable inert solvents such as benzene, toluene and xylene may be optionally used even when a carboxylic acid is used as the organic acid. The reaction goes to completion at approximately room temperature to reflux temperature of the solvent for about 10–80 hours to provide the compound (11).

Examples of the lower alkyl having oxo and represented by $\Phi$ in the compound (11) include those prepared by eliminating protective groups from the corresponding "lower alkyl having protected oxo" and represented by Ψ. Specific examples are formyl, formylmethyl, acetyl, 2-formylethyl, 2-oxopropyl, propionyl, 3-formylpropyl, 3-oxobutyl, 2-oxobutyl, butyryl, 4-formylbutyl, 4-oxopentyl, 3-oxopentyl, 2-oxopentyl, valeryl, 5-formylpentyl, 5-oxohexyl, 4-oxohexyl, 3-oxohexyl, 2-oxohexyl, hexanoyl, and the like.

The subsequent reduction of the compound (11) can be carried out using a suitable reducing agent in an inert solvent. Examples of useful reducing agents are borohydride compounds such as sodium borohydride, potassium borohydride, lithium borohydride, sodium cyanoborohydride and sodium triethylborohydride, and lithium aluminum hydride compounds such as lithium aluminum hydride and lithium tributoxyaluminohydride. When a borohydride compound is used as the reducing agent, the inert solvent is preferably either an alcohol solvent such as methanol and ethanol or a mixed solvent of said alcohol and another solvent such as dichloromethane and diethyl ether. When a lithium aluminum hydride compound is used as the reducing agent, the solvent is preferably diethyl ether, THF or like ethers. The reducing agent is preferably used in at least approximately equimolar proportion relative to the compound (11). The reaction goes to completion at approximately 0° C. to room temperature in about 0.5–3 hours.

Acylation of the compound (12) thus obtained can be carried out using an acylating agent in the absence of solvents or in an inert solvent such as pyridine, lutidine, N,N-dimethylformamide (DMF) and N,N-dimethylacetoamide (DMA). Examples of useful acylating agents are acid anhydrides such as acetic anhydride, propionic anhydride, butyric anhydride, valeric anhydride, hexanoic anhydride and heptanoic anhydride. These are generally used in an amount of 1–10 equivalents relative to the compound (12). In order not to acylate hydroxyl at 7 position of the compound (12), the reaction conditions are preferably selected within the ranges of approximately 0° C. to room temperature and of about 0.5 to 2 hours.

Halogenation of the compound (13) thus obtained can be carried out in the same manner as the halogenation of the compound (4) in Reaction Scheme-1.

Conversion of the compound (14) thus obtained to the compound (15) can be carried out under the same conditions as in the conversion of the compound (5) to the compound (6) in Reaction Scheme-1. The lower alkyl having acyloxy and represented by Σ in the compound (14) is hydrolyzed to form hydroxy(lower)alkyl by this reaction.

Silylation of the compound (15) thus obtained can be carried out using halotrialkylsilane in the presence of an acid acceptor in a suitable inert solvent such as THF and dichloromethane. Examples of useful acid acceptors are sodium carbonate, potassium carbonate, triethylamine and N,N-dimethylaminopyridine. Examples of useful halotrialkylsilane are chlorotrimethylsilane, chlorotriethylsilane, chlorotripropylsilane, chlorotributylsilane and chlorobutyldiethylsilane. These are normally used in an approximately equimolar to excessive amount relative to the compound (15). The reaction goes to completion at approximately room temperature in about 5–30 hours.

Lastly the compound (16) thus obtained is reacted with acid halide (7) to provide the desired compound (1b) of the invention. This reaction can be carried out in the same manner as the reaction using acid halide (7) in Reaction Scheme-1. The substituent Ω at position 5 of the compound (16) can be easily converted to the corresponding $R^{1b}$ group (hydroxy(lower)alkyl) by this reaction or the subsequent hydrolysis.

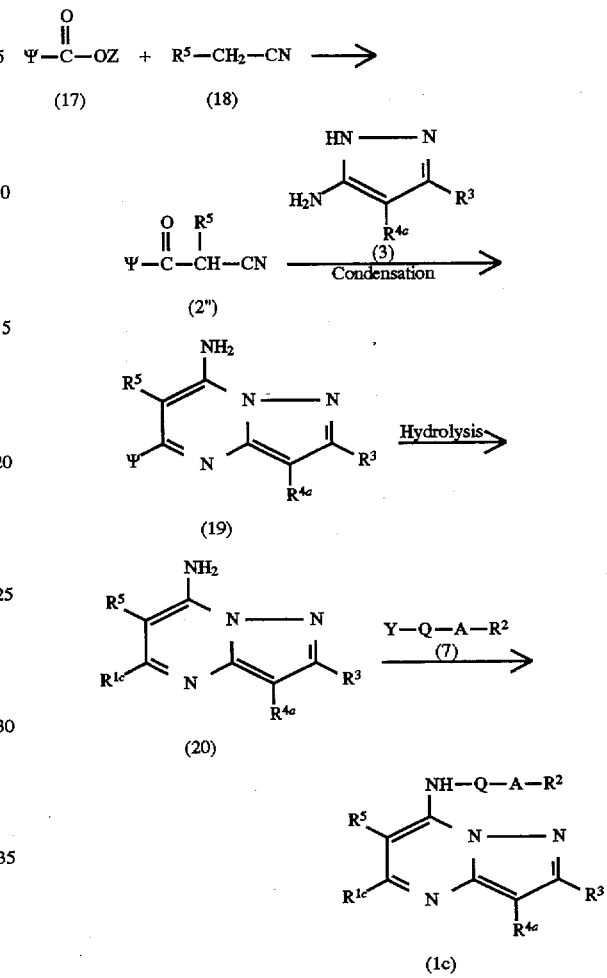

wherein $R^2$, $R^3$, $R^{4a}$, $R^5$, X, Y, Z, Q, A, n and Ψ are as defined above and $R^{1c}$ is lower alkyl having oxo.

The reaction of the compound (17) and the nitrile derivative (18) in Reaction Scheme-3 can be carried out in an inert solvent such as DMF, DMA and dimethyl sulfoxide (DMSO) in the presence of a base such as sodium hydride and potassium hydride. The nitrile derivative (18) and the base are preferably used in an amount of 1 to an excessive equivalent relative to the compound (17) respectively. The reaction goes to completion at approximately 0° C. to room temperature in 2–10 hours.

The subsequent condensation of the compounds (2") and (3) can be carried out in the same manner as the condensation in Reaction Scheme-1'.

Hydrolysis of the compound (19) can be carried out in the same manner as the hydrolysis in Reaction Scheme-2.

The reaction of the compounds (20) and (7) can be carried out in the same manner as the reaction in Reaction Scheme-1.

[Reaction Scheme-4]

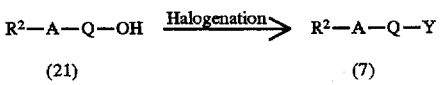

wherein $R^2$, A, Q and Y are as defined above.

As shown in Reaction Scheme-4, acid halide (7) to be used in Reaction Schemes-1, 2 and 3 can be prepared by halogenating the compound (21). The halogenation can be carried out by a conventional method. For example, the compound (21) is reacted with a halogenating agent such as thionyl chloride and thionyl bromide in the absence of solvents or in an inert solvent such as chloroform and diethylether. In this method, an excess of the halogenating agent is generally used. The reaction can be carried out at approximately room temperature to 150° C. for about 0.5–5 hours.

[Reaction Scheme-5]

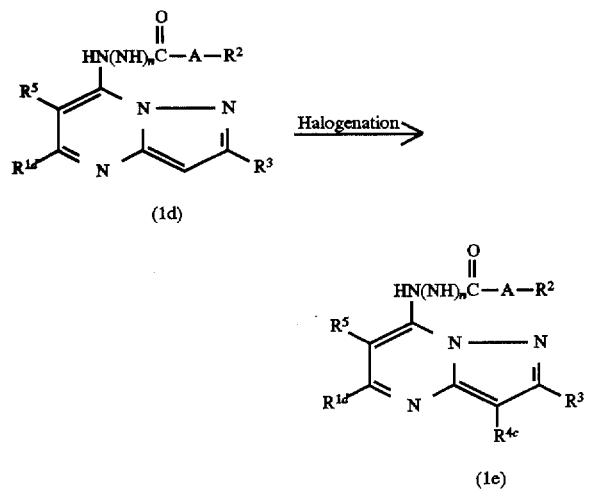

wherein $R^2$, $R^3$, $R^5$, A and n are as defined above, $R^{1d}$ is hydrogen, lower alkyl which may have lower alkyoxy or lower alkylthio as a substituent, cycloalkyl, thienyl, furyl, or phenyl which may have 1–3 substituents selected from the group consisting of lower alkyl, lower alkoxy, phenylthio and halogen, $R^{1d}$ and $R^5$ may conjointly form lower alkylene and $R^{4c}$ is halogen.

The halogenation of the compound (1d) in Reaction Scheme-5 can be carried out using a halogenating agent such as N-bromosuccinimide (NBS) and N-chlorosuccinimide (NCS) in an inert solvent such as benzene, carbon tetrachloride and chloroform. The halogenating agent is normally used in an amount of 1 equivalent to a slightly excessive amount relative to the compound (1d). The reaction can be carried out at approximately room temperature to reflux temperature of the solvent for 0.5–5 hours.

[Reaction Scheme-6]

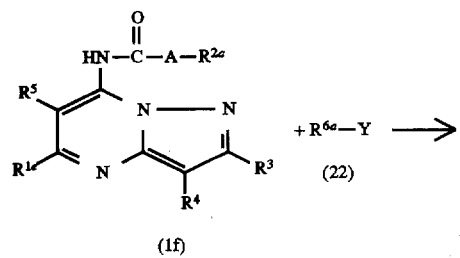

-continued
[Reaction Scheme-6]

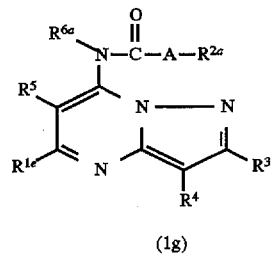

wherein $R^3$, $R^4$, $R^5$ and Y are as defined above, $R^{1e}$ is hydrogen, lower alkyl which may have thienyl, lower alkoxy, lower alkylthio or oxo as an substituent, cycloalkyl, thienyl, furyl, lower alkenyl, or phenyl which may have 1–3 substituents selected from the group consisting of lower alkyl, lower alkoxy, phenylthio and halogen, $R^{1e}$ and $R^5$ may conjointly form lower alkylene, $R^{2a}$ is naphthyl, cycloalkyl, furyl, thienyl, optionally halogen-substituted pyridyl, optionally halogen-substituted phenoxy, or phenyl which may have 1–3 substituents selected from the group consisting of lower alkyl, lower alkoxy, halogen, nitro, halogen-substituted lower alkyl, halogen-substituted lower alkoxy, lower alkoxycarbonyl, phenyl(lower)alkoxy, cyano, lower alkanoyloxy, phenyl and di(lower)alkoxyphosphoryl-(lower)alkyl, and $R^{6a}$ is phenyl(lower)alkyl, or benzoyl having 1–3 substituents selected from the group consisting of lower alkoxy, halogen-substituted lower alkyl and halogen.

In Reaction Scheme-6, the compound (1f) is reacted with the compound (22) in an inert solvent in the presence of a base to provide the compound (1g). When $R^{6a}$ is a phenyl (lower)alkyl, suitable inert solvents are DMF, DMA, DMSO, etc. and suitable bases are sodium hydride, potassium hydride, etc. When $R^{6a}$ is a benzoyl having 1–3 substituents selected from the group consisting of lower alkoxy, halogen-substituted lower alkyl and halogen, suitable inert solvents are chloroform, dichloromethane, etc. and suitable bases are triethylamine, N,N-dimethylaniline, etc. The compound (22) is normally used in an amount of 1 to a slightly excessive equivalent. The base is preferably used in an amount of 1 to an excessive equivalent. The reaction is carried out at approximately 0° C. to room temperature for 3–30 hours.

[Reaction Scheme-7]

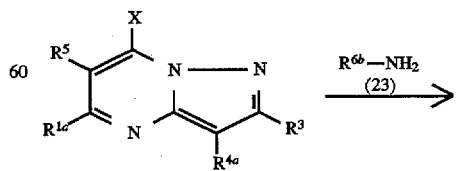

-continued
[Reaction Scheme-7]

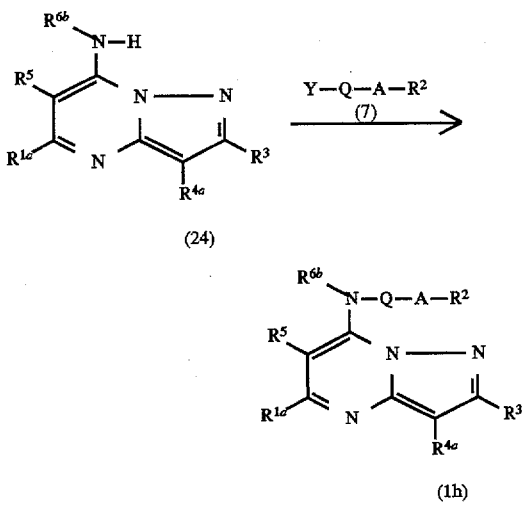

wherein $R^{1a}$, $R^2$, $R^3$, $R^{4a}$, $R^5$, X, Y, Q and A are as defined above and $R^{6b}$ is lower alkyl or phenyl(lower)alkyl.

The reaction of the compounds (5) and (23) in Reaction Scheme-7 is carried out in an inert solvent such as methanol and ethanol in the presence of an acid acceptor such as sodium hydrogen carbonate, sodium carbonate and potassium carbonate at reflux temperature of the solvent for about 1–5 hours.

The reaction of the compounds (24) and (7) can be carried out in the same manner as the corresponding reaction in Reaction Scheme-1, thus giving the compound (1h).

[Reaction Scheme-8]

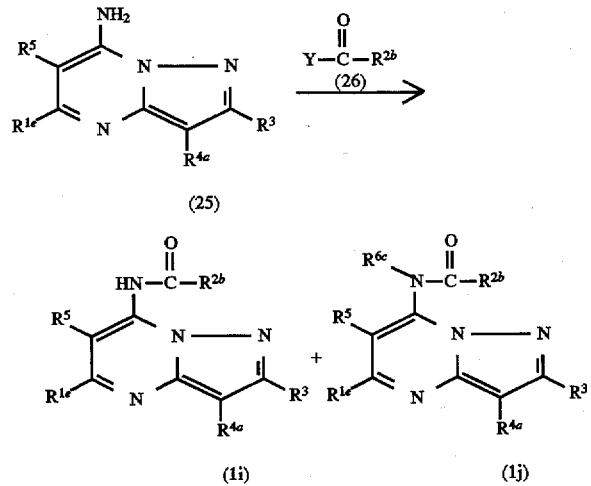

wherein $R^{1e}$, $R^3$, $R^{4a}$, $R^5$, and Y are as defined above, $R^{2b}$ is phenyl having 1–3 substituents selected from the group consisting of lower alkoxy, halogen, halogen-substituted lower alkyl and $R^{6c}$ is benzoyl having 1 to 3 substituents selected from the group consisting of lower alkoxy, halogen-substituted lower alkyl and halogen.

The reaction of the compounds (25) and (26) in Reaction Scheme-8 can be carried out in the same manner as the reaction of the compounds (6) and (7) in Reaction Scheme-1. A by-product (1j) is obtained together with the main product (1i) by this reaction.

The compounds of the invention can be formed into pharmaceutically acceptable acid addition salts, which are also included among the compounds of the invention. The acid for use to form such salts includes inorganic acids such as hydrochloric acid, hydrobromic acid and sulfuric acid and organic acids such as oxalic acid, fumaric acid, maleic acid, tartaric acid and citric acid. The reaction for forming such salts can be performed by conventional methods.

The object compound in each of the above processes can be easily isolated by conventional separation and purification means. Examples of useful isolation means include various conventional means such as adsorption chromatography, preparative thin-layer chromatography, recrystallization and solvent extraction.

Some compounds of formula (1) according to the invention, wherein A is alkenylene or $R^1$ is lower alkenyl, may be cis- or trans-isomers. Of course, these isomers are included in the invention.

Compounds of the formula (1) according to the invention may exist as optical isomers having an carbon atom as a stereogenic center. Such optically active substances and racemic derivatives are included in the invention.

The compound of the invention can be made into usual dosage forms of pharmaceutical compositions using suitable non-toxic pharmaceutically acceptable carriers. The present invention provides such pharmaceutical compositions, especially analgesics.

Examples of useful pharmaceutically acceptable carriers include conventional diluents or excipients such as fillers, volume builders, binders, humectants, disintegrators, surfactants, lubricants, and the like. These carriers are selectively used according to the desired unit dosage form.

The unit dosage form of said pharmaceutical composition can be selected from a broad variety of forms according to the intended medical treatment. Typical examples are tablets, pills, powders, solutions, suspensions, emulsions, granules, capsules, suppositories, injections (solutions, suspensions, etc.), ointments, and the like.

The tablets can be molded using as pharmaceutically acceptable carriers excipients such as lactose, sucrose, sodium chloride, glucose, urea, starch, calcium carbonate, kaolin, crystalline cellulose, silicic acid and potassium phosphate, binders such as water, ethanol, propanol, simple syrup, glucose syrup, starch solution, gelatin solution, carboxymethyl cellulose, hydroxypropyl cellulose, methyl cellulose and polyvinyl pyrrolidone, disintegrators such as sodium carboxymethyl cellulose, calcium carboxymethyl cellulose, low-substituted hydroxypropyl cellulose, dry starch, sodium alginate, agar powder, laminaran powder, sodium hydrogen carbonate and calcium carbonate, surfactants such as polyoxyethylene sorbitan fatty acid ester, sodium lauryl sulfate and stearyl monoglyceride, disintegration inhibitors such as sucrose, stearin, cacao butter and hydrogenated oil, absorption promoters such as quaternary ammonium base and sodium lauryl sulfate, humectants such as glycerin and starch, adsorbents such as starch, lactose, kaolin, bentonite and colloidal silicic acid, and lubricants such as purified talc, stearic acid salt, boric acid powder and polyethylene glycol. Furthermore, such tablets may be optionally coated to provide sugar-coated tablets, gelatin-coated tablets, enteric tablets, film-coated tablets, etc. or be processed into double-layer or multiple-layer tablets.

The pills can be molded using as pharmaceutically acceptable carriers excipients such as glucose, lactose, starch, cacao butter, hydrogenated vegetable oil, kaolin and talc, binders such as gum arabic powder, tragacanth powder, gelatin and ethanol, and disintegrators such as laminaran and starch.

The suppositories can be molded using as pharmaceutically acceptable carriers polyethylene glycol, cacao butter, higher alcohols or their esters, gelatin, semisynthetic glycerides, and the like.

The capsules can be manufactured by mixing the active ingredient compound of the invention with pharmaceutically acceptable carriers as mentioned above and filling the mixture into hard gelatin capsule shells, soft capsule shells, etc. according to conventional methods.

The injections in the form of solutions, emulsions, suspensions, etc. can be manufactured using diluents such as water, ethyl alcohol, macrogol, propylene glycol, ethoxylated isostearyl alcohol, polyoxyisostearyl alcohol and polyoxyethylene sorbitan fatty acid ester and are preferably sterilized and rendered isotonic with respect to the blood. In order to provide such an isotonic solution, a sufficient amount of sodium chloride, glucose or glycerin may be added to the pharmaceutical composition of the invention. Conventional solubilizers, buffers, local anesthetics, etc. may also be added.

Further, coloring agents, preservatives, perfumes, flavors, sweeteners, or other pharmaceutical compositions may be optionally incorporated in the pharmaceutical compositions of the invention.

The ointments in the form of paste, cream, gel, etc. can be manufactured using diluents such as white vaseline, paraffin, glycerin, cellulose derivatives, polyethylene glycol, silicone and bentonire.

The proportion of the active ingredient compound of formula (1) of the invention in the pharmaceutical composition of the invention is not so critical but can be liberally selected from a broad range. Generally, the active ingredient compound preferably accounts for about 1 to 70 weight % of the final composition.

There is no specific limitation on the administration method for the pharmaceutical composition of the invention. The proper method can be determined according to the dosage form, patient's age, sex or other conditions, severity of disease, etc. For example, the tablets, pills, solutions, suspensions, emulsions, granules and capsules are orally administered. The injections are intravenously administered singly or in admixture with a conventional infusion such as glucose and amino acid, and optionally administered singly by the intramuscular, intradermal, subcutaneous or intraperitoneal route. The suppositories are intrarectally administered.

The dosage of the pharmaceutical composition is suitably selected according to the administration method, patient's age, sex or other conditions, severity of disease, etc. The dosage of the compound of the invention as the active ingredient is preferably about 0.5–20 mg per kg body weight a day and this amount can be administered once or in 2–4 divided doses.

BEST MODE FOR PRACTICING THE INVENTION

Preparation examples for starting compounds to produce compounds of the invention are given below as Reference Examples, and preparation examples for compounds of the invention are given below as Examples to clarify the present invention in more detail.

REFERENCE EXAMPLE 1

Preparation of 7-amino-5-n-butylpyrazolo[1,5-a]pyrimidine

Step (1)

A solution of 100 g of 3-aminopyrazole and 190 g of methyl 3-oxoheptanoate in 120 ml of toluene was refluxed with heating at 100° C. for 3 hours and then cooled. Toluene was distilled off under reduced pressure and diethyl ether was added to the residue. The crystals precipitated were collected and washed with diethyl ether and acetonitrile to provide 184 g of 5-n-butyl-7-hydroxypyrazolo[1,5-a]pyrimidine as colorless crystals.

Step (2)

Phosphorus oxychloride (80 ml) and triethylamine (44 ml) were added to a toluene suspension (400 ml) containing 40 g of the crystals obtained in step (1). The reaction mixture was refluxed with heating for 4 hours. After completion of the reaction, the reaction mixture was concentrated under reduced pressure and the residue was poured into ice water. The mixture was neutralized with sodium acetate and extracted with ethyl acetate. The organic layer was collected, washed with a saturated saline solution, dried over anhydrous sodium sulfate and concentrated under reduced pressure. The residue was purified by silica gel column chromatography (eluent: ethyl acetate: n-hexane=1:9) to provide 41 g of 5-n-butyl-7-chloropyrazolo[1,5-a]pyrimidine as a light yellow oily compound.

Step (3)

The compound prepared in the above step (2) (21 g) and 25% aqueous ammonia (100 ml) were enclosed in a stainless steel sealed tube, heated at 110° C. for 12 hours and cooled. The crystals precipitated were collected by filtration, washed with water and recrystallized from chloroform-n-hexane to provide 18.4 g of 7-amino-5-n-butylpyrazolo[1,5-a]pyrimidine as colorless crystals (melting point: 124°–126° C.).

The following compounds were prepared in the same manner as above.

(1) 7-Amino-5-ethylpyrazolo[1,5-a]pyrimidine (melting point: 175°–177° C., recrystallization solvent: ethyl acetate-n-hexane)

(2) 7-Amino-5-n-propylpyrazolo[1,5-a]pyrimidine (melting point: 138°–140° C., recrystallization solvent: ethyl acetate-n-hexane)

(3) 7-Amino-5-cyclopropylpyrazolo[1,5-a]pyrimidine (melting point: 206°–209° C., recrystallization solvent: chloroform-n-hexane)

(4) 7-Amino-5-n-pentylpyrazolo[1,5-a]pyrimidine (melting point: 125°–126° C., recrystallization solvent: ethyl acetate-n-hexane)

(5) 7-Amino-5-phenylpyrazolo[1,5-a]pyrimidine (melting point: 207°–209° C., recrystallization solvent: ethyl acetate-n-hexane)

(6) 7-Amino-5-(4-methoxyphenyl)pyrazolo[1,5-a]pyrimidine (melting point: 194°–196° C., recrystallization solvent: ethanol-n-hexane)

(7) 7-Amino-5-(2-thienyl)pyrazolo[1,5-a]pyrimidine (melting point: 227°–229° C., recrystallization solvent: ethanol-n-hexane)

(8) 7-Amino-5-(3-thienyl)pyrazolo[1,5-a]pyrimidine (melting point: 203°–205° C., recrystallization solvent: ethanol-n-hexane)

(9) 7-Amino-5-methylpyrazolo[1,5-a]pyrimidine (melting point: 220°–222° C., recrystallization solvent: chloroform-n-hexane)

(10) 7-Amino-5-n-butyl-2-methylpyrazolo[1,5-a]pyrimidine (melting point: 176°–178° C., recrystallization solvent: chloroform-n-hexane)

(11) 7-Amino-5-(2,4-dimethylphenyl)pyrazolo[1,5-a]pyrimidine (melting point: 168°–170° C., recrystallization solvent: chloroform-n-hexane)

(12) 7-Amino-5-(3,5-dimethylphenyl)pyrazolo[1,5-a]pyrimidine (melting point: 180°–182° C., recrystallization solvent: ethanol-n-hexane)

(13) 7-Amino-5-(2-methoxyphenyl)pyrazolo[1,5-a] pyrimidine (melting point: 201°–203° C., recrystallization solvent: ethanol-n-hexane)
(14) 7-Amino-5-(3-methoxyphenyl)pyrazolo[1,5-a] pyrimidine (melting point: 195°–197° C., recrystallization solvent: ethanol-n-hexane)
(15) 7-Amino-5-(3,4,5-trimethoxyphenyl)pyrazolo[1,5-a] pyrimidine (melting point: 198°–200° C., recrystallization solvent: ethanol-n-hexane)
(16) 7-Amino-5-(2-chlorophenyl)pyrazolo[1,5-a]pyrimidine (melting point: 208°–210° C., recrystallization solvent: chloroform-n-hexane)
(17) 7-Amino-5-(2-furyl)pyrazolo[1,5-a]pyrimidine (melting point: 204°–206° C., recrystallization solvent: ethanol-n-hexane)
(18) 7-Amino-5-(3-furyl)pyrazolo[1,5-a]pyrimidine (melting point: 208°–210° C., recrystallization solvent: ethanol-n-hexane)
(19) 7-Amino-5-(2-thienylmethyl)pyrazolo[1,5-a] pyrimidine (melting point: 188°–190° C., recrystallization solvent: ethanol-n-hexane)
(20) 7-Amino-5-(3,5-dimethoxyphenyl)pyrazolo[1,5-a] pyrimidine (melting point: 207°–209° C., recrystallization solvent: ethanol-n-hexane)

The following compounds were also prepared in the same manner as above.

(21) 7-Amino-5-(3-butenyl)pyrazolo[1,5-a]pyrimidine
(22) 7-Amino-5-ethoxymethylpyrazolo[1,5-a]pyrimidine
(23) 7-Amino-5-(2-methylphenyl)pyrazolo[1,5-a] pyrimidine
(24) 7-Amino-5-(3-methylphenyl)pyrazolo[1,5-a] pyrimidine
(25) 7-Amino-5-(4-methylphenyl)pyrazolo[1,5-a] pyrimidine
(26) 7-Amino-5-(3-chlorophenyl)pyrazolo[1,5-a]pyrimidine
(27) 7-Amino-5-(4-chlorophenyl)pyrazolo[1,5-a]pyrimidine
(28) 7-Aminopyrazolo[1,5-a]pyrimidine
(29) 7-Amino-5-n-butyl-3-ethoxycarbonyl-2-methylpyrazolo[1,5-a]pyrimidine (melting point: 178°–180° C., recrystallization solvent: methylene chloride-n-hexane)
(30) 7-Amino-2,5-di-n-butyl-3-methylpyrazolo[1,5-a] pyrimidine (melting point: 123°–125° C., recrystallization solvent: diethyl ether-n-hexane)
(31) 7-Amino-5-n-butyl-2-phenylpyrazolo[1,5-a]pyrimidine (melting point: 206°–208° C., recrystallization solvent: ethyl acetate-n-hexane)
(32) 7-Amino-3-benzyl-5-n-butyl-2-phenylpyrazolo[1,5-a] pyrimidine (melting point: 106°–108° C., recrystallization solvent: chloroform-n-hexane)
(33) 7-Amino-5-n-butyl-2-phenyl-3-[4-(phenylthio) phenyl] pyrazolo[1,5-a]pyrimidine (melting point: 139°–141° C., recrystallization solvent: diethyl ether-n-hexane)
(34) 7-Amino-3,5-di-n-butylpyrazolo[1,5-a]pyrimidine (melting point: 58°–60° C., recrystallization solvent: ethyl acetate-n-hexane)
(35) 7-Amino-5-n-butyl-3-phenylpyrazolo[1,5-a]pyrimidine (melting point: 113°–115° C., recrystallization solvent: ethyl acetate-n-hexane)
(36) 7-Amino-5-[(ethylthio)methyl]pyrazolo[1,5-a] pyrimidine (melting point: 109°–111° C., recrystallization solvent: chloroform-n-hexane)
(37) 7-Amino-5-[2-(methylthio)ethyl]pyrazolo[1,5-a] pyrimidine (melting point: 77°–79° C., recrystallization solvent: ethyl acetate-n-hexane)
(38) 7-Amino-5-[4-(phenylthio)phenyl]pyrazolo[1,5-a] pyrimidine (melting point: 182°–184° C., recrystallization solvent: chloroform-diethyl ether)
(39) 9-Amino-5,6,7,8-tetrahydropyrazolo[5,1-b]quinazoline (melting point: 230°–233° C., recrystallization solvent: ethyl acetate-n-hexane)
(40) 7-Amino-2,5-di-n-butylpyrazolo[1,5-a]pyrimidine (melting point: 105°–107° C., recrystallization solvent: diethyl ether-n-hexane)

REFERENCE EXAMPLE 2

Preparation of 5-n-butyl-7-hydrazinopyrazolo[1,5-a] pyrimidine

Hydrazine monohydrate (50 ml) was slowly added dropwise to 21.0 g of 5-n-butyl-7-chloropyrazolo[1,5-a] pyrimidine prepared in step (2) of Reference Example 1 at room temperature and stirred at room temperature for 10 hours. After completion of the reaction, the crystals precipitated were collected, washed with water and recrystallized from chloroform-n-hexane to provide 12.6 g of the object compound as colorless crystals (melting point: 126°–129° C.).

7-Hydrazino-5-phenylpyrazolo[1,5-a]pyrimidine was prepared in the same manner as above.

REFERENCE EXAMPLE 3

Preparation of 7-amino-5-(3-oxobutyl)pyrazolo[1,5-a]pyrimidine

An acetonitrile solution (10 ml) containing 5.0 g of methyl 2-methyl-1,3-dioxolane-2-propionate was added dropwise to 10 ml of a DMF suspension containing 2.3 g of 60% sodium hydride, and stirred at room temperature for 4 hours. The reaction mixture was poured into ice water, acidified with a saturated citric acid solution and extracted with ethyl acetate. The organic layer was washed with water and a saturated saline solution and concentrated under reduced pressure. The residue was purified by silica gel column chromatography (eluent: n-hexane:ethyl acetate= 3:2) to provide 3.0 g of 2-methyl-β-oxo-1,3-dioxolane-2-pentanenitrile as oil.

Subsequently, a toluene solution (1.6 ml) containing 3.0 g of the compound thus obtained and 1.4 g of 3-aminopyrazole was stirred at 115° C. for 10 hours. The reaction mixture was concentrated under reduced pressure. The residue was purified by silica gel column chromatography (eluent: chloroform:methanol=20:1) and recrystallized from chloroform-n-hexane to provide 2.1 g of 7-amino-5-[2-(2-methyl-1,3-dioxolane-2-yl) ethyl]pyrazolo[1,5-a]pyrimidine as colorless crystals.

Then 1.0 g of the crystals thus obtained were dissolved in 500 ml of acetic acid-water (4:1) and stirred at 80° C. overnight. After completion of the reaction, the reaction mixture was concentrated under reduced pressure. The remaining acetic acid-water was azeotropically distilled off with benzene. The residue was recrystallized from ethanol-n-hexane to provide 0.7 g of the title object compound as colorless crystals.

Melting point: 164°–166° C., recrystallization solvent: ethanol-n-hexane

REFERENCE EXAMPLE 4

Preparation of 7-amino-5-n-butyl-6-methylpyrazolo [1,5-a]pyrimidine

A toluene solution (2.5 ml) containing 1.8 g of 3-aminopyrazole and 3 g of 2-methyl-3-oxoheptanenitrile was heated at 115° C. for 3.5 hours. Toluene was distilled off under reduced pressure and the residue was recrystallized from ethyl acetate and washed with diethyl ether to provide 2.4 g of the title object compound as colorless crystals.

Melting point: 153°–155° C., recrystallization solvent: ethyl acetate

EXAMPLE 1

Preparation of 5-n-butyl-7-(3,4,5-trimethoxybenzoylamino) pyrazolo[1,5-a]pyrimidine 7-Amino-5-n-butylpyrazolo[1,5-a]pyrimidine (1.90 g) and pyridine (20 ml) were dissolved in 20 ml of dry dichloromethane. A dry dichloromethane solution (10 ml) containing 2.6 g of 3,4,5-trimethoxybenzoyl chloride was slowly added dropwise thereto and stirred at room temperature for 10 hours. After addition of 50 ml of a 10% aqueous sodium hydrogen carbonate solution, the reaction mixture was extracted with chloroform. The organic layer was collected, washed with 10% aqueous hydrochloric acid and water, dried over anhydrous sodium sulfate and concentrated under reduced pressure. The residue was purified by silica gel column chromatography (eluent: ethyl acetate: n-hexane=1:2) and recrystallized from diethyl ether-n-hexane to provide 2.4 g of the object compound as colorless crystals. Table 1 shows the structure and melting point of the compound obtained.

EXAMPLES 2–46

The compounds set forth in Table 1 were prepared in the same manner as in Example 1. The structures and melting points of the compounds are also shown in Table 1. As to the oily compounds, data on the results of $^1$H-NMR analysis are shown.

EXAMPLES 47–99

The compounds set forth in Table 2 were prepared in the same manner as in Example 1. The structures and melting points of the compounds are also shown in Table 2. As to the oily compounds, data on the results of $^1$H-NMR analysis are shown.

EXAMPLE 100

Preparation of 5-(3-hydroxybutyl)-7-(3,4,5-trimethoxybenzoylamino) pyrazolo[1,5-a]pyrimidine Step (1)

A toluene solution (2 ml) containing 0.90 g of 3-aminopyrazole and 1.90 g of methyl 2-methyl-β-oxo-1,3-dioxolane-2-valerate was refluxed with heating at 115° C. for 1 hour, allowed to cool and then concentrated under reduced pressure. Diethyl ether was added to the residue. The crystals precipitated were collected and washed with diethyl ether to provide 1.85 g of 7-hydroxy-5-[2-(2-methyl-1,3-dioxolane-2-yl)ethyl]pyrazolo[1,5-a]pyrimidine as colorless crystals.

Step (2)

The crystals thus obtained (2.2 g) were dissolved in 500 ml of acetic acid-water (4:1) and stirred at 50° C. for 3 days. After completion of the reaction, the reaction mixture was concentrated under reduced pressure and the remaining acetic acid-water was azeotropically distilled off with benzene. The residue was recrystallized from ethanol-n-hexane to provide 11.0 g of 7-hydroxy-5-(3-oxobutyl)pyrazolo[1,5-a]pyrimidine as colorless crystals.

Step (3)

The crystals obtained in step (2) (5.7 g) were dissolved in 120 ml of methanol. Sodium borohydride (0.53 g) was added under ice-cooling and stirred at 0° C. for 2 hours. After completion of the reaction, the reaction mixture was acidified by adding dilute aqueous hydrochloric acid dropwise and then extracted with chloroform. The organic layer was collected, washed with a saturated saline solution, dried over anhydrous sodium sulfate and concentrated under reduced pressure. The residue was recrystallized from ethanol-n-hexane to provide 4.16 g of 7-hydroxy-5-(3-hydroxybutyl) pyrazolo[1,5-a]pyrimidine as colorless crystals.

Step (4)

The crystals obtained in step (3) (4.16 g) were dissolved in 40 ml of acetic anhydride and 40 ml of pyridine and stirred at room temperature for 30 minutes. After completion of the reaction, the reaction mixture was concentrated under reduced pressure and the residue was recrystallized from methanol-diethyl ether to provide 4.2 g of 5-(3-acetoxybutyl)-7-hydroxypyrazolo[1,5-a]pyrimidine as colorless crystals.

Step (5)

Phosphorus oxychloride (6.4 ml) and triethylamine (3.5 ml) were added to 40 ml of a toluene suspension containing 4.2 g of the crystals obtained in step (4), and the mixture was refluxed with heating for 6 hours. After completion of the reaction, the reaction mixture was concentrated under reduced pressure and the residue was poured into ice water. The mixture was neutralized with sodium acetate and extracted with ethyl acetate. The organic layer was collected, washed with a saturated saline solution, dried over anhydrous sodium sulfate and concentrated under reduced pressure. The residue was purified by silica gel column chromatography (eluent: ethyl acetate: n-hexane=4:1) to provide 4.3 g of 5-(3-acetoxybutyl)-7-chloropyrazolo[1,5-a] pyrimidine as a light yellow oily compound.

Step (6)

The compound prepared in step (5) (4.3 g) and 25% aqueous ammonia (50 ml) were enclosed in a stainless steel sealed tube, heated at 105° C. for 14 hours and allowed to cool. The crystals precipitated were collected by filtration, washed with water and dried to provide 3.2 g of 7-amino-5-(3-hydroxybutyl)pyrazolo[1,5-a]pyrimidine as light yellow crystals.

Step (7)

Triethylamine (400 µl) and chlorotrimethylsilane (680 µl) were added to 5 ml of a THF solution containing 500 mg of the crystals obtained in step (6), and the mixture was stirred at room temperature for 12 hours. After completion of the reaction, a saturated aqueous NaHCO$_3$ solution was added and the reaction mixture was extracted with dichloromethane. The organic layer was collected, washed with water and a saturated saline solution, dried over anhydrous sodium sulfate and concentrated under reduced pressure. n-Hexane was added to the residue. The crystals precipitated were collected by filtration to provide 520 mg of 7-amino-5-(3-trimethylsilyloxybutyl) pyrazolo[1,5-a]pyrimidine as colorless crystals.

$^1$H-NMR (δ:ppm) [CDCl$_3$]0.12(9H, s), 1.20 (3H, d, J=5.9), 1.8–1.9 (2H, m), 2.6–2.9 (2H, m), 3.8–3.9 (1H, m), 5.61 (2H, brs), 5.99 (1H, s), 6.41 (1H, d, J=2.0), 7.99 (1H, d, J=2.0)

Step (8)

A dry dichloromethane solution (5 ml) containing 650 mg of 3,4,5-trimethoxybenzoyl chloride was slowly added dropwise to 5 ml of a pyridine solution containing 520 mg of the crystals obtained in step (7), and stirred at room temperature for 2 hours. After completion of the reaction, a saturated aqueous NaHCO$_3$ solution was added and the reaction mixture was extracted with dichloromethane. The organic layer was collected and washed with a 1N aqueous hydrochloric acid until the pH of the water layer became about 1. The organic layer was allowed to stand for 2 hours, washed with water and a saturated saline solution, dried over anhydrous sodium sulfate and concentrated under reduced pressure. The residue was recrystallized from dichloromethane-n-hexane to provide 480 mg of the object compound as colorless crystals. Table 2 shows the structure and melting point of the compound obtained.

EXAMPLES 101 and 102

The compounds set forth in Table 2 were prepared in the same manner as in Example 100. The structures and melting points of the compounds are also shown in Table 2.

EXAMPLE 103

Preparation of 5-n-butyl-3-chloro-2-methyl-7-(3,4,5-trimethoxybenzoylamino) pyrazolo[1,5-a]pyrimidine 5-n-Butyl-2-methyl-7-(3,4,5-trimethoxybenzoyl-amino) pyrazolo[1,5-a]pyrimidine (the compound of Example 53; 0.78 g) was dissolved in 10 ml of chloroform. After addition of 0.28 g of NCS, the mixture was refluxed with heating for 1 hour and allowed to cool. After addition of some water, the reaction mixture was extracted with chloroform. The organic layer was collected, dried over anhydrous sodium sulfate and concentrated under reduced pressure. The residue was purified by silica gel column chromatography (eluent: ethyl acetate:n-hexane=1:2) and recrystallized from ethanol-n-hexane to provide 0.61 g of the object compound as colorless crystals. Table 3 shows the structure and melting point of the compound obtained.

EXAMPLES 104–106

The compounds set forth in Table 3 were prepared in the same manner as in Example 103. The structures and melting points of the compounds are also shown in Table 3.

EXAMPLES 107–128

The compounds set forth in Table 4 were prepared in the same manner as in Example 1. The structures and melting points of the compounds are also shown in Table 4.

EXAMPLE 129

Preparation of 5-n-butyl-7-[N-methyl-N-(3,4,5-trimethoxybenzoyl) amino]pyrazolo[1,5-a]pyrimidine 5-n-Butyl-7-chloropyrazolo[1,5-a]pyrimidine (the compound prepared in step (2) of Reference Example 1; 8.60 g), sodium hydrogen carbonate (3.44 g) and 40% methylamine (3.18 g) were added to 50 ml of ethanol and heated at 120° C. for 2 hours. After completion of the reaction, ethanol was distilled off under reduced pressure. After addition of some water, the residue was extracted with ethyl acetate. The organic layer was collected, dried over anhydrous sodium sulfate and concentrated under reduced pressure. The residue was purified by silica gel column chromatography (eluent: ethyl acetate:n-hexane=1:2) to provide 2.33 g of 5-n-butyl-7-methylaminopyrazolo[1,5-a]pyrimidine as crystals.

The object compound was prepared using the crystals thus obtained and 3,4,5-trimethoxybenzoyl chloride in the same manner as in Example 1. The structure and melting point of the compound obtained are shown in Table 5.

EXAMPLE 130

The compound set forth in Table 5 was prepared in the same manner as in Example 129. The structure and melting point of the compound are also shown in Table 5.

EXAMPLE 131

Preparation of 5-n-butyl-7-[N,N-bis 3,4,5-trimethoxybenzoyl) amino]pyrazolo[1,5-a] pyrimidine The compound prepared in Example 1 (1.92 g) and triethylamine (1.02 g) were dissolved in 10 ml of chloroform. A chloroform solution (10 ml) containing 1.28 g of 3,4,5-trimethoxybenzoyl chloride was added to the solution at room temperature and the mixture was stirred at room temperature for 10 hours. After completion of the reaction, the organic layer was washed with dilute aqueous hydrochloric acid, dried over anhydrous sodium sulfate and concentrated. The residue was purified by silica gel column chromatography (eluent: ethyl acetate:n-hexane=1:2) and recrystallized from ethyl acetate-n-hexane to provide 1.10 g of the object compound as colorless crystals.

The structure and melting point of the compound obtained are shown in Table 5.

EXAMPLE 132

Preparation of 5-n-butyl-7-[N,N-bis(2-chlorobenzoyl) amino]pyrazolo[1,5-a]pyrimidine The former fractions obtained by silica gel column chromatography in Example 23 were purified by silica gel column chromatography again (eluent: dichloromethane), and recrystallized to provide the object compound as colorless crystals. Table 5 shows the structure and melting point of the compound obtained.

EXAMPLES 133–134

The former fractions obtained by silica gel column chromatography in Examples 32 and 52 were treated in the same manner as in Example 132, thus giving the compounds shown in Table 5. The structures and melting points of the compounds are also shown in Table 5.

The former fractions obtained by silica gel column chromatography in Example 1 were treated likewise, giving the same compound as in Example 131.

TABLE 1

[Structure: core scaffold with NHC(=O)-A-R² substituent on a pyrazolo-pyrimidine ring system bearing R¹]

Me: methyl group, Et: ethyl group, nPr: n-propyl group,
nBu: n-butyl group, nPe: n-pentyl group, Ph: phenyl group

| Example No. | R¹ | R² | A | Melting point (°C.) (Recrystallization solvent) |
|---|---|---|---|---|
| 1 | nBu | 3,4,5-trimethoxyphenyl (OMe, OMe, OMe) | Single-bond | 127~129 (Diethyl ether-n-hexane) |
| 2 | nBu | Ph | Single-bond | 83~85 (Ethyl acetate-n-hexane) |
| 3 | nBu | 2-methylphenyl (o-Me-C₆H₄) | Single-bond | 102~104 (n-Hexane) |
| 4 | nBu | 3-methylphenyl (m-Me-C₆H₄) | Single-bond | 94~95 (n-Hexane) |
| 5 | nBu | 4-methylphenyl (p-Me-C₆H₄) | Single-bond | 83~84 (n-Hexane) |
| 6 | nBu | 4-tert-butylphenyl (p-C(Me)₃-C₆H₄) | Single-bond | $^1$H-NMR(CDCl₃) 0.97(3H, t, J=7.3), 1.37(9H, s), 1.4–1.5(2H, m), 1.7–1.9(2H, m), 2.86(2H, t, J=7.8), 6.57(1H, d, J=2.3), 7.58(1H, d, J=8.7), 7.77 (1H, s), 7.97(1H, d, J=8.7), 8.03 (1H, d, J=2.3), 10.0(1H, brs) |
| 7 | nBu | 2-methoxyphenyl (o-MeO-C₆H₄) | Single-bond | 82~84 (n-Hexane) |
| 8 | nBu | 3-methoxyphenyl (m-OMe-C₆H₄) | Single-bond | 49~51 (n-Hexane) |
| 9 | nBu | 4-methoxyphenyl (p-OMe-C₆H₄) | Single-bond | 108~109 (n-Hexane) |

TABLE 1-continued

Structure:
$$\text{NHC(=O)-A-R}^2$$ attached to a bicyclic ring system with R¹ substituent (pyrazolo-pyrimidine scaffold shown)

Me: methyl group, Et: ethyl group, nPr: n-propyl group,
nBu: n-butyl group, nPe: n-pentyl group, Ph: phenyl group

| Example No. | R¹ | R² | A | Melting point (°C.) (Recrystallization solvent) |
|---|---|---|---|---|
| 10 | nBu | 2,3-(MeO)₂-phenyl | Single-bond | 129~132 (n-Hexane) |
| 11 | nBu | 3,4-(OMe)₂-phenyl | Single-bond | 143~144 (Diethyl ether-n-hexane) |
| 12 | nBu | 2,6-(MeO)₂-phenyl | Single-bond | 101~103 (Diethyl ether-n-hexane) |
| 13 | nBu | 3,5-(OMe)₂-phenyl | Single-bond | 92~94 (Diethyl ether-n-hexane) |
| 14 | nBu | 2,3,4-(MeO)₃-phenyl | Single-bond | 115~117 (Ethyl acetate-n-hexane) |
| 15 | Et | 3,4,5-(OMe)₃-phenyl | Single-bond | 141~143 (Ethyl acetate-n-hexane) |
| 16 | nPr | 3,4,5-(OMe)₃-phenyl | Single-bond | 119~121 (Diethyl ether-n-hexane) |
| 17 | cyclopropyl | 3,4,5-(OMe)₃-phenyl | Single-bond | 198~201 (Ethyl acetate-n-hexane) |

TABLE 1-continued

Structure:

NHC(=O)—A—R² attached to a pyrazolo-pyrimidine type heterocycle with R¹ substituent.

Me: methyl group, Et: ethyl group, nPr: n-propyl group,
nBu: n-butyl group, nPe: n-pentyl group, Ph: phenyl group

| Example No. | R¹ | R² | A | Melting point (°C.) (Recrystallization solvent) |
|---|---|---|---|---|
| 18 | nPe | 3,4,5-tri(OMe)-phenyl | Single-bond | 116~118 (n-Hexane) |
| 19 | Ph | 3,4,5-tri(OMe)-phenyl | Single-bond | 185~187 (Ethyl acetate-n-hexane) |
| 20 | nBu | 3,4,5-tri(OEt)-phenyl | Single-bond | 100~102 (Diethyl ether-n-hexane) |
| 21 | nBu | 4-(O-nBu)-phenyl | Single-bond | 87~90 (n-Hexane) |
| 22 | nBu | 2-F-phenyl | Single-bond | 99~100 (n-Hexane) |
| 23 | nBu | 2-Cl-phenyl | Single-bond | 107~109 (Diethyl ether) |
| 24 | nBu | 3-Cl-phenyl | Single-bond | 81~82 (n-Hexane) |
| 25 | nBu | 4-Cl-phenyl | Single-bond | 92~94 (Diethyl ether) |

TABLE 1-continued

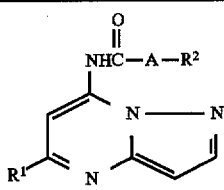

Me: methyl group, Et: ethyl group, nPr: n-propyl group,
nBu: n-butyl group, nPe: n-pentyl group, Ph: phenyl group

| Example No. | R¹ | R² | A | Melting point (°C.) (Recrystallization solvent) |
|---|---|---|---|---|
| 26 | nBu | 2,4-dichlorophenyl | Single-bond | 97~99 (n-Hexane) |
| 27 | nBu | 3-bromophenyl | Single-bond | 93~95 (n-Hexane) |
| 28 | nBu | 4-bromophenyl | Single-bond | 97~99 (n-Hexane) |
| 29 | nBu | 2-nitrophenyl | Single-bond | 133~135 (Ethyl acetate-n-hexane) |
| 30 | nBu | 3-nitrophenyl | Single-bond | 143~145 (Ethyl acetate-n-hexane) |
| 31 | Et | 2-(trifluoromethyl)phenyl | Single-bond | 125~127 (Diethyl ether-n-hexane) |
| 32 | nBu | 2-(trifluoromethyl)phenyl | Single-bond | 84~87 (n-Hexane) |
| 33 | nBu | 4-(trifluoromethyl)phenyl | Single-bond | 95~97 (n-Hexane) |
| 34 | nBu | 4-(methoxycarbonyl)phenyl | Single-bond | 122~123 (n-Hexane) |
| 35 | nBu | 4-biphenylyl | Single-bond | 139~141 (Ethyl acetate-n-hexane) |

TABLE 1-continued

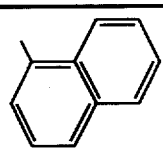

Me: methyl group, Et: ethyl group, nPr: n-propyl group,
nBu: n-butyl group, nPe: n-pentyl group, Ph: phenyl group

| Example No. | R¹ | R² | A | Melting point (°C.) (Recrystallization solvent) |
|---|---|---|---|---|
| 36 | nBu | 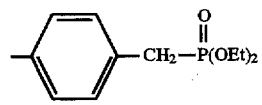 | Single-bond | 119–121 (Ethyl acetate-n-hexane) |
| 37 | nBu | 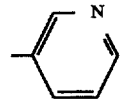 | Single-bond | 57–60 (Ethyl acetate-n-hexane) |
| 38 | nBu | 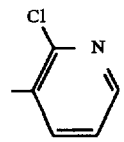 | Single-bond | 82–84 (Diethyl ether-n-hexane) |
| 39 | nBu | 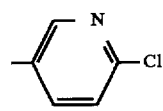 | Single-bond | 103–105 (Ethyl acetate-n-hexane) |
| 40 | nBu | 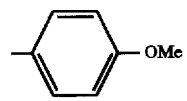 | Single-bond | 92–93 (Diethyl ether-n-hexane) |
| 41 | nBu | Ph | —CH$_2$— | 80–82 (Diethyl ether-n-hexane) |
| 42 | nBu | 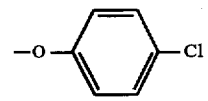 | —CH$_2$— | 73–75 (Diethyl ether-n-hexane) |
| 43 | nBu | Ph | —C$_2$H$_4$— | $^1$H-NMR(CDCl$_3$) 0.95(3H, t, J=7.3), 1.3–1.5 (2H, m), 1.7–1.8(2H, m), 2.80 (2H, t, J=7.8), 2.88(2H, t, J= 7.5), 3.09(2H, t, J=7.5), 6.53 (1H, d, J=2.2), 7.2–7.3(5H, m), 7.60(1H, s), 7.95(1H, d, J=2.2), 9.23(1H, brs) |
| 44 | nBu | PhO— | —CH$_2$— | 108–109 (n-Hexane) |
| 45 | nBu | 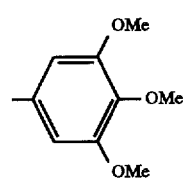 | —CH$_2$— | 140–142 (Ethyl acetate-n-hexane) |
| 46 | nBu |  | —CH=CH— | 134–137 (Ethyl acetate-n-hexane) |

TABLE 2

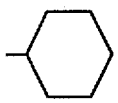

Me: methyl group, Et: ethyl group, nPr: n-propyl group,
nBu: n-butyl group, tBu: t-butyl group, nPe: n-pentyl group,
Ph: phenyl group, Ac: acetyl group

| No. | R¹ | R² | R³ | A | n | Melting point (°C.) (Recrystallization solvent) |
|---|---|---|---|---|---|---|
| 47 | nBu | 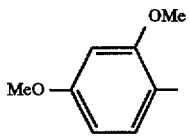 | H | Singlebond | 0 | ¹H-NMR(CDCl₃)0.95(3H, t, J=7.4), 1.2-2.1(14H, m), 2.4-2.6(1H, m), 2.81(2H, t, J=7.8), 6.54(1H, d, J=2.2), 7.62(1H, s), 8.00(1H, d, J=2.2), 9.29(1H, brs) |
| 48 | nBu | 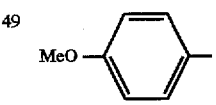 | H | Singlebond | 0 | 141~142 (Ethanol-n-hexane) |
| 49 | 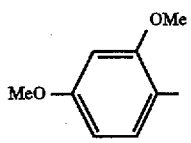 | 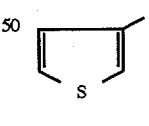 | H | Singlebond | 0 | 209~211 (Methylene chloride-ethyl acetate) |
| 50 | 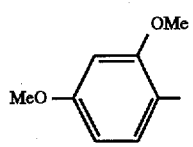 | 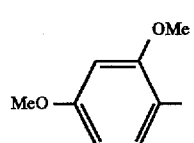 | H | Singlebond | 0 | 206~208 (Methylene chloride-ethyl acetate) |
| 51 | nBu | 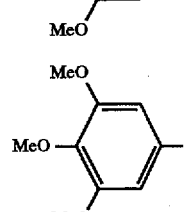 | H | Singlebond | 0 | 136~137 (Ethanol-n-hexane) |
| 52 | Me | 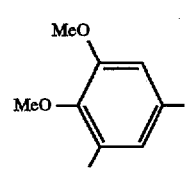 | H | Singlebond | 0 | 173~175 (Ethanol-n-hexane) |
| 53 | nBu | 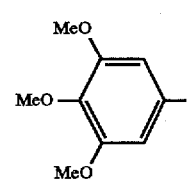 | Me | Singlebond | 0 | 127~129 (Ethanol-n-hexane) |
| 54 | CH₂=CH—C₂H₄— | 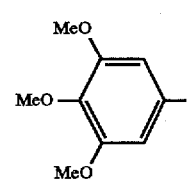 | H | Singlebond | 0 | 104~106 (Ethyl acetate-n-hexane) |

TABLE 2-continued

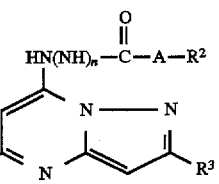

Me: methyl group, Et: ethyl group, nPr: n-propyl group,
nBu: n-butyl group, tBu: t-butyl group, nPe: n-pentyl group,
Ph: phenyl group, Ac: acetyl group

| No. | $R^1$ | $R^2$ | $R^3$ | A | n | Melting point (°C.) (Recrystallization solvent) |
|---|---|---|---|---|---|---|
| 55 | Et—O—CH$_2$— | 3,4,5-(MeO)$_3$-C$_6$H$_2$— | H | Singlebond | 0 | 138~140 (Ethyl acetate-n-hexane) |
| 56 | 2-Me-C$_6$H$_4$— | 3,4,5-(MeO)$_3$-C$_6$H$_2$— | H | Singlebond | 0 | 163~165 (Chloroform-ethyl acetate) |
| 57 | 3-Me-C$_6$H$_4$— | 3,4,5-(MeO)$_3$-C$_6$H$_2$— | H | Singlebond | 0 | 166~168 (Ethyl acetate-n-hexane) |
| 58 | 4-Me-C$_6$H$_4$— | 3,4,5-(MeO)$_3$-C$_6$H$_2$— | H | Singlebond | 0 | 193~195 (Methylene chloride-diethyl ether) |
| 59 | 2,4-Me$_2$-C$_6$H$_3$— | 3,4,5-(MeO)$_3$-C$_6$H$_2$— | H | Singlebond | 0 | 174~176 (Methylene chloride-diethyl ether) |
| 60 | 3,5-Me$_2$-C$_6$H$_3$— | 3,4,5-(MeO)$_3$-C$_6$H$_2$— | H | Singlebond | 0 | 203~205 (Methylene chloride-diethyl ether) |
| 61 | 2-MeO-C$_6$H$_4$— | 3,4,5-(MeO)$_3$-C$_6$H$_2$— | H | Singlebond | 0 | 175~177 (Methylene chloride-ether acetate) |

TABLE 2-continued

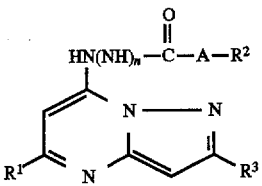

Me: methyl group, Et: ethyl group, nPr: n-propyl group,
nBu: n-butyl group, tBu: t-butyl group, nPe: n-pentyl group,
Ph: phenyl group, Ac: acetyl group

| No. | $R^1$ | $R^2$ | $R^3$ | A | n | Melting point (°C.) (Recrystallization solvent) |
|---|---|---|---|---|---|---|
| 62 | 3-MeO-phenyl | 2,3-(MeO)₂-phenyl | H | Singlebond | 0 | 192–194 (Methylene chloride-diethyl ether) |
| 63 | 4-MeO-phenyl | 2,3-(MeO)₂-phenyl | H | Singlebond | 0 | 181–183 (Methylene chloride-diethyl ether) |
| 64 | 3,5-(MeO)₂-phenyl | 2,3-(MeO)₂-phenyl | H | Singlebond | 0 | 224–226 (Methylene chloride-diethyl ether) |
| 65 | 3,4,5-(MeO)₃-phenyl | 2,3-(MeO)₂-phenyl | H | Singlebond | 0 | 214–216 (Methylene chloride-diethyl ether) |
| 66 | 2-Cl-phenyl | 2,3-(MeO)₂-phenyl | H | Singlebond | 0 | 190–192 (Methylene chloride-diethyl ether) |
| 67 | 3-Cl-phenyl | 2,3-(MeO)₂-phenyl | H | Singlebond | 0 | 222–224 (Chloroform-ethyl acetate) |
| 68 | 4-Cl-phenyl | 2,3-(MeO)₂-phenyl | H | Singlebond | 0 | 193–195 (Chloroform-ethyl acetate) |

TABLE 2-continued

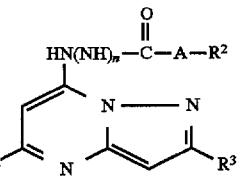

Me: methyl group, Et: ethyl group, nPr: n-propyl group,
nBu: n-butyl group, tBu: t-butyl group, nPe: n-pentyl group,
Ph: phenyl group, Ac: acetyl group

| No. | $R^1$ | $R^2$ | $R^3$ | A | n | Melting point (°C.) (Recrystallization solvent) |
|---|---|---|---|---|---|---|
| 69 | (2-furyl) | 3,4,5-(MeO)$_3$-C$_6$H$_2$- | H | Singlebond | 0 | 189–191 (Methylene chloride-diethyl ether) |
| 70 | (3-furyl) | 3,4,5-(MeO)$_3$-C$_6$H$_2$- | H | Singlebond | 0 | 174–176 (Methylene chloride-ethyl acetate) |
| 71 | (2-thienyl) | 3,4,5-(MeO)$_3$-C$_6$H$_2$- | H | Singlebond | 0 | 191–193 (Methylene chloride-diethyl ether) |
| 72 | (3-thienyl) | 3,4,5-(MeO)$_3$-C$_6$H$_2$- | H | Singlebond | 0 | 198–200 (Methylene chloride-ethyl acetate) |
| 73 | (2-thienyl)-CH$_2$- | 3,4,5-(MeO)$_3$-C$_6$H$_2$- | H | Singlebond | 0 | 157–159 (Ethyl acetate) |
| 74 | nBu | 3-HO-4,5-(MeO)$_2$-C$_6$H$_2$- | H | Singlebond | 0 | 159–161 (Ethanol-n-hexane) |
| 75 | nBu | 3-EtO-4,5-(MeO)$_2$-C$_6$H$_2$- | H | Singlebond | 0 | 79–81 (Diethyl ether-n-hexane) |

TABLE 2-continued $$\text{structure: HN(NH)}_n\text{-C(=O)-A-R}^2 \text{ attached to pyrazole ring system with R}^1 \text{ and R}^3$$

Me: methyl group, Et: ethyl group, nPr: n-propyl group,
nBu: n-butyl group, tBu: t-butyl group, nPe: n-pentyl group,
Ph: phenyl group, Ac: acetyl group

| No. | $R^1$ | $R^2$ | $R^3$ | A | n | Melting point (°C.) (Recrystallization solvent) |
|---|---|---|---|---|---|---|
| 76 | nBu | 2,6-(MeO)$_2$-4-(nBuO)-phenyl | H | Singlebond | 0 | 98~100 (n-Hexane) |
| 77 | nBu | 2,6-(MeO)$_2$-4-(PhCH$_2$O)-phenyl | H | Singlebond | 0 | 82~85 (Ethanol-n-hexane) |
| 78 | nBu | 2,6-(MeO)$_2$-4-(AcO)-phenyl | H | Singlebond | 0 | 158~160 (Ethyl acetate-n-hexane) |
| 79 | nBu | 2,6-(MeO)$_2$-4-Br-phenyl | H | Singlebond | 0 | 182~184 (Ethyl acetate-n-hexane) |
| 80 | nBu | 2,6-Cl$_2$-4-MeO-phenyl | H | Singlebond | 0 | 132~135 (Ethyl acetate-n-hexane) |
| 81 | nBu | 2-Cl-3,6-(MeO)$_2$-phenyl | H | Singlebond | 0 | 111~113 (Diethyl ether-n-hexane) |
| 82 | Me | 2-CF$_3$-phenyl | H | Singlebond | 0 | 154~155 (Ethanol-n-hexane) |

TABLE 2-continued $$\text{HN(NH)}_n-\overset{\overset{\displaystyle O}{\|}}{\text{C}}-\text{A}-\text{R}^2$$

(structure: pyrazolo-pyrimidine core with R¹ and R³ substituents)

Me: methyl group, Et: ethyl group, nPr: n-propyl group,
nBu: n-butyl group, tBu: t-butyl group, nPe: n-pentyl group,
Ph: phenyl group, Ac: acetyl group

| No. | R¹ | R² | R³ | A | n | Melting point (°C.) (Recrystallization solvent) |
|---|---|---|---|---|---|---|
| 83 | nPr | 2-(CF₃)phenyl | H | Singlebond | 0 | 139~141 (Diethyl ether-n-hexane) |
| 84 | cyclopropyl | 2-(CF₃)phenyl | H | Singlebond | 0 | 102~104 (n-Hexane) |
| 85 | nPe | 2-(CF₃)phenyl | H | Singlebond | 0 | 93~95 (n-Hexane) |
| 86 | Ph | 2-(CF₃)phenyl | H | Singlebond | 0 | 143~145 (Diethyl ether-n-hexane) |
| 87 | nBu | 3-(CF₃)phenyl | H | Singlebond | 0 | 46~48 (Ethyl acetate-n-hexane) |
| 88 | nBu | 2,4-bis(CF₃)phenyl | H | Singlebond | 0 | 108~110 (n-Hexane) |
| 89 | nBu | 3,5-bis(CF₃)phenyl | H | Singlebond | 0 | 92.5~94.5 (n-Hexane) |
| 90 | nBu | 2-(NH₂)phenyl | H | Singlebond | 0 | 106~108 (n-Hexane) |

TABLE 2-continued

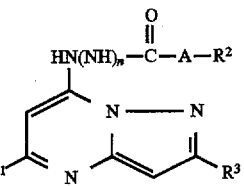

Me: methyl group, Et: ethyl group, nPr: n-propyl group,
nBu: n-butyl group, tBu: t-butyl group, nPe: n-pentyl group,
Ph: phenyl group, Ac: acetyl group

| No. | $R^1$ | $R^2$ | $R^3$ | A | n | Melting point (°C.) (Recrystallization solvent) |
|---|---|---|---|---|---|---|
| 91 | nBu | 4-NC-C6H4- | H | Singlebond | 0 | 123~125 (Ethanol-n-hexane) |
| 92 | nBu | 2-pyridyl | H | Singlebond | 0 | 123~125 (Diethyl ether-n-hexane) |
| 93 | nBu | 4-pyridyl | H | Singlebond | 0 | 139~140 (Ethanol-n-hexane) |
| 94 | nBu | 3,4,5-(MeO)3-C6H2- | H | $CH_2$ | 0 | 121~123 (ethyl acetate-n-hexane) |
| 95 | nBu | 4-Ph-C6H4- | H | $-CH=CH-$ | 0 | 194~196 (Ethanol-n-hexane) |
| 96 | nBu | 3,4,5-(MeO)3-C6H2- | H | Singlebond | 1 | 222 (Decomposition) (Ethanol-n-hexane) |
| 97 | Ph | 3,4,5-(MeO)3-C6H2- | H | Singlebond | 1 | 250 (Decomposition) (Methanol-n-hexane) |
| 98 | nBu | 2-CF3-C6H4- | H | Singlebond | 1 | 247 (Decomposition) (Ethanol-n-hexane) |
| 99 | Ph | 2-CF3-C6H4- | H | Singlebond | 1 | 263 (Decomposition) (Ethanol-n-hexane) |

TABLE 2-continued

[Structure: HN(NH)ₙ—C(=O)—A—R² substituted pyrazolo-pyrimidine core with R¹ and R³ groups]

Me: methyl group, Et: ethyl group, nPr: n-propyl group,
nBu: n-butyl group, tBu: t-butyl group, nPe: n-pentyl group,
Ph: phenyl group, Ac: acetyl group

| No. | R¹ | R² | R³ | A | n | Melting point (°C.) (Recrystallization solvent) |
|---|---|---|---|---|---|---|
| 100 | CH₃—CH(OH)—C₂H₄— | 3,4,5-(MeO)₃-C₆H₂— | H | Singlebond | 0 | 128~130 (Methylene chloride-n-hexane) |
| 101 | CH₃—CH(OH)—C₂H₄— | 3-MeO,4-OH,5-MeO-C₆H₂— | H | Singlebond | 0 | 153~155 (Ethanol-n-hexane) |
| 102 | CH₃—CH(OH)—C₂H₄— | 3-MeO,4-OCH₂Ph,5-MeO-C₆H₂— | H | Singlebond | 0 | 127~129 (Ethyl acetate-n-hexane) |

TABLE 3

[Structure: HN(NH)ₙ—C(=O)—A—R² substituted pyrazolo-pyrimidine core with R¹, R³ and R⁴ groups]

Me: methy group, nBu: n-butyl group

| Ex. No. | R¹ | R² | R³ | R⁴ | A | n | Melting point (°C.) (Recrystallization solvent) |
|---|---|---|---|---|---|---|---|
| 103 | nBu | 3,4,5-(MeO)₃-C₆H₂— | Me | Cl | Singlebond | 0 | 106~108 (Ethanol-n-hexane) |
| 104 | nBu | 3,4,5-(MeO)₃-C₆H₂— | H | Cl | Singlebond | 0 | 142~143 (Ethanol-n-hexane) |

TABLE 3-continued

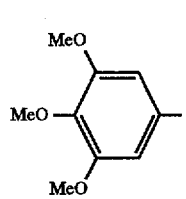

Me: methyl group, nBu: n-butyl group

| Ex. No. | R¹ | R² | R³ | R⁴ | A | n | Melting point (°C.) (Recrystallization solvent) |
|---|---|---|---|---|---|---|---|
| 105 | nBu | MeO-, MeO-, MeO- phenyl | H | Br | Single-bond | 0 | 146~148 (Ethanol-n-hexane) |
| 106 | nBu | F₃C-phenyl | H | Cl | Single-bond | 0 | 133~135 (Diethyl ether-n-hexane) |

TABLE 4

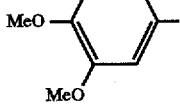

Me: methyl group, Et: ethyl group, nBu: n-butyl group, Ph: phenyl group

| Ex. No. | R¹ | R⁵ | R² | R³ | R⁴ | Q | A* | n | Melting point (°C.) (reclystallization solvent) |
|---|---|---|---|---|---|---|---|---|---|
| 107 | H | H | MeO-,MeO-,MeO- phenyl | H | H | $\overset{O}{\underset{\|}{C}}$ | SB | 0 | 185~187 (Methylene chloride-n-hexane) |
| 108 | nBu | H | MeO-,MeO-,MeO- phenyl | Me | $\overset{O}{\underset{\|}{-COEt}}$ | $\overset{O}{\underset{\|}{C}}$ | SB | 0 | 138~140 (Ethyl acetate-n-hexane) |
| 109 | nBu | H | MeO-,MeO-,MeO- phenyl | nBu | H | $\overset{O}{\underset{\|}{C}}$ | SB | 0 | 95~97 (Ethyl acetate-n-hexane) |

TABLE 4-continued $$\text{HN(NH)}_n-\text{Q}-\text{A}-\text{R}^2$$ attached to pyrazine ring system with R¹, R³, R⁴, R⁵ substituents Me: methyl group, Et: ethyl group, nBu: n-butyl group, Ph: phenyl group

| Ex. No. | R¹ | R⁵ | R² | R³ | R⁴ | Q | A* | n | Melting point (°C.) (recrystallization solvent) |
|---|---|---|---|---|---|---|---|---|---|
| 110 | nBu | H | 3,4,5-(MeO)₃-C₆H₂- | nBu | Me | C=O | SB | 0 | 96–98 (Ethyl acetate-n-hexane) |
| 111 | nBu | H | 3,4,5-(MeO)₃-C₆H₂- | Ph | H | C=O | SB | 0 | 190–192 (Methylene chloride-diethyl ether) |
| 112 | nBu | H | 3,4,5-(MeO)₃-C₆H₂- | Ph | PhCH₂— | C=O | SB | 0 | 149–151 (Ethyl acetate-n-hexane) |
| 113 | nBu | H | 3,4,5-(MeO)₃-C₆H₂- | Ph | PhS-C₆H₄- | C=O | SB | 0 | 111–113 (Ethyl acetate-n-hexane) |
| 114 | nBu | H | 3,4,5-(MeO)₃-C₆H₂- | H | nBu | C=O | SB | 0 | 81–83 (n-Hexane) |
| 115 | nBu | H | 3,4,5-(MeO)₃-C₆H₂- | H | Ph | C=O | SB | 0 | 139–141 (Ethyl acetate-n-hexane) |
| 116 | nBu | Me | 3,4,5-(MeO)₃-C₆H₂- | H | H | C=O | SB | 0 | 145–147 (Methylene chloride-n-hexane) |

TABLE 4-continued

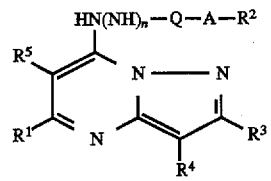

Me: methyl group, Et: ethyl group, nBu: n-butyl group, Ph: phenyl group

| Ex. No. | R¹ | R⁵ | R² | R³ | R⁴ | Q | A* | n | Melting point (°C.) (reclystallization solvent) |
|---|---|---|---|---|---|---|---|---|---|
| 117 | —CH₂CH₂CH₂CH₂— | | 3,4,5-tri(MeO)-phenyl | H | H | O=C | SB | 0 | 102~104 (Methylene chloride-n-hexane) |
| 118 | Me—C(=O)—CH₂CH₂— | H | 3,4,5-tri(MeO)-phenyl | H | H | O=C | SB | 0 | 115~117 (Methylene chloride-n-hexane) |
| 119 | Et—S—CH₂— | H | 3,4,5-tri(MeO)-phenyl | H | H | O=C | SB | 0 | 80~82 (Ethyl acetate-n-hexane) |
| 120 | MeS—CH₂CH₂— | H | 3,4,5-tri(MeO)-phenyl | H | H | O=C | SB | 0 | 113~115 (Methylene chloride-diethyl ether) |
| 121 | PhS-phenyl- | H | 3,4,5-tri(MeO)-phenyl | H | H | O=C | SB | 0 | 179~181 (Methylene chloride-diethyl ether) |
| 122 | nBu | H | 2-Br-phenyl | H | H | O=C | SB | 0 | 98~100 (Diethyl ether) |
| 123 | nBu | H | 4-OCF₃-phenyl | H | H | O=C | SB | 0 | 73~75 (n-Hexane) |
| 124 | nBu | H | 2,4-bis(CF₃)-phenyl | H | H | O=C | SB | 0 | 129~131 (n-Hexane) |

TABLE 4-continued

[Structure: HN(NH)ₙ—Q—A—R² substituted pyrazolo-pyrimidine with R¹, R³, R⁴, R⁵]

Me: methyl group, Et: ethyl group, nBu: n-butyl group, Ph: phenyl group

| Ex. No. | R¹ | R⁵ | R² | R³ | R⁴ | Q | A* | n | Melting point (°C.) (reclystallization solvent) |
|---|---|---|---|---|---|---|---|---|---|
| 125 | nBu | H | 2-furyl | H | H | C(=O) | SB | 0 | 91–93 (Diethyl ether-n-hexane) |
| 126 | nBu | H | 2-thienyl | H | H | C(=O) | SB | 0 | 91–93 (n-Hexane) |
| 127 | nBu | H | Ph | H | H | SO₂ | SB | 0 | >300° C. (Ethyl acetate-n-hexane) |
| 128 | nBu | H | 2,4-dichlorophenyl | H | H | SO₂ | SB | 0 | >300° C. (Ethyl acetate-n-hexane) |

*In column A. "SB" means "Single bond".

TABLE 5

[Structure: R⁶N(—C(=O)—A—R²) substituted pyrazolo-pyrimidine with R¹, R³, R⁴, R⁵]

Me: methyl group, nBu: n-butyl group

| Ex. No. | R¹ | R⁵ | R² | R³ | R⁴ | R⁶ | A* | Melting point (°C.) (Reclystallization solvent) |
|---|---|---|---|---|---|---|---|---|
| 129 | nBu | H | 3,4,5-trimethoxyphenyl (MeO, MeO, MeO) | H | H | Me | SB | 93–95 (Ethyl acetate-n-hexane) |
| 130 | nBu | H | 3,4,5-trimethoxyphenyl (MeO, MeO, MeO) | H | H | Ph-CH₂— | SB | ¹H-NMR(CDCl₃) 0.76(3H, t, J=7.2), 0.9–1.1(2H, m), 1.3–1.4(2H, m), 2.51(2H, t, J=7.4), 3.47(6H, s), 3.74(3H, s), 5.33(2H, brs), 5.83 (1H, s), 6.60(2H, s), 6.68(1H, d, J=2.0), 7.1–7.3(5H, m), 8.24(1H, d, J=2.0) |

TABLE 5-continued

Me: methyl group, nBu: n-butyl group

| Ex. No. | R¹ | R⁵ | R² | R³ | R⁴ | R⁶ | A* | Melting point (°C.) (Reclystallization solvent) |
|---|---|---|---|---|---|---|---|---|
| 131 | nBu | H | 3,4,5-tri(MeO)-phenyl | H | H | 2,4,6-tri(OMe)-benzoyl | SB | 127–129 (Ethyl acetate-n-hexane) |
| 132 | nBu | H | Cl (2-chlorophenyl) | H | H | 2-chlorobenzoyl | SB | 119–121 (Diethyl ether-n-hexane) |
| 133 | Me | H | 3,4,5-tri(MeO)-phenyl | H | H | 2,4,6-tri(OMe)-benzoyl | SB | 180–182 (Methylene chloride-n-hexane) |
| 134 | nBu | H | 3-(CF₃)-phenyl | H | H | 3-(CF₃)-benzoyl | SB | 111–113 (Diethyl ether-n-hexane) |

*In column A, "SB" means "Single bond".

Given below are Pharmacological Test Examples for the compounds of the invention and Formulation Examples for pharmaceutical compositions containing the compounds of the invention.

Pharmacological Test Example 1

Six-week-old male Wistar rats were used as subjects (each group: 7 rats). The pain threshold of each rat's left hind paw was measured using Analgesy-Meter (Unicom) based on the method of Randall-Selitto [Randall, L. O. and Selitto, J. J., Arch. Int. Pharmacodyn., 111, 409 (1957)]. The value thus obtained was termed "pre-value".

After one hour from the measurement, 0.1 ml of a 20% yeast suspension was subcutaneously injected to the left hind paw of each rat. Immediately after the injection, a 5% gum arabic suspension containing the compound of the invention was orally given to the rats of test group in an amount of 10 ml/kg, whereas a 5% gum arabic suspension (free of the compound of the invention) was given to the rats of control group likewise.

The pain threshold of each rat's left hind paw was measured in the same manner as mentioned above every one hour after the yeast injection. The value thus obtained was termed "post-value".

The recovery rate of the pain threshold was calculated from these values (post-values) and the pre-values of the rats in each group, by means of the following formula.

Recovery rate of pain threshold (%) =

$$\frac{(\text{Test group average post-value}) - (\text{Control group average post-value})}{(\text{Control group average pre-value}) - (\text{Control group average post-value})} \times 100$$

Table 6 shows the results (the highest recovery rates).

TABLE 6

| Ex. No. | Recovery rate (%) | Dosage (mg/kg) | Time to measure (hours later) |
|---|---|---|---|
| 1 | 41.5 | 3 | 3 |
| 7 | 44.1 | 3 | 4 |
| 14 | 51.6 | 3 | 4 |
| 19 | 53.9 | 3 | 3 |
| 21 | 54.0 | 3 | 4 |
| 23 | 45.1 | 3 | 1 |
| 32 | 43.0 | 3 | 3 |

TABLE 6-continued

| Ex. No. | Recovery rate (%) | Dosage (mg/kg) | Time to measure (hours later) |
|---|---|---|---|
| 36 | 32.7 | 1 | 3 |
| 48 | 52.2 | 1 | 3 |
| 52 | 79.6 | 3 | 3 |
| 54 | 55.7 | 1 | 4 |
| 55 | 73.7 | 3 | 3 |
| 69 | 38.7 | 1 | 3 |
| 70 | 36.8 | 1 | 3 |
| 74 | 43.9 | 1 | 2 |
| 76 | 57.6 | 1 | 2 |
| 77 | 41.6 | 1 | 3 |
| 79 | 32.1 | 1 | 3 |
| 88 | 76.4 | 3 | 4 |
| 92 | 39.7 | 1 | 3 |
| 93 | 32.6 | 1 | 4 |
| 94 | 31.3 | 1 | 3 |
| 96 | 35.0 | 1 | 2 |
| 97 | 51.5 | 1 | 4 |
| 104 | 78.5 | 3 | 3 |
| 111 | 62.0 | 3 | 4 |
| 115 | 61.0 | 3 | 4 |
| 120 | 63.8 | 3 | 4 |
| 121 | 46.2 | 3 | 3 |
| 127 | 36.4 | 1 | 3 |
| 134 | 115.4 | 3 | 3 |

PHARMACOLOGICAL TEST EXAMPLE 2

Using 6-week-old male Wistar rats (each group: 7 rats), the pain threshold of each rat's left hind paw was measured using Analgesy-Meter (Unicom) based on the method of Randall-Selitto [Randall, L. O. and Selitto, J. J., Arch. Int. Pharmacodyn., 111, 409 (1957)]. The value thus obtained was termed "pre-value".

After one hour from the measurement, a 5% gum arabic suspension containing the compound of the invention was orally given to the rats of test group in an amount of 10 ml/kg so that the dosage of the compound of the invention was 1 mg/kg, whereas a 5% gum arabic suspension (free of the compound of the invention) was given to the rats of control group likewise. One hour later, a physiological saline solution containing substance P (25 ng/0.1 ml) was subcutaneously injected to the left hind paw of each rat.

The pain threshold of each rat's left hind paw was measured in the same manner as above at a certain time after the injection of substance P. The value thus obtained was termed "post-value".

The recovery rate of the pain threshold was calculated from these values (post-values) and the pre-values of the rats in each group, by means of the following formula.

Recovery rate of pain threshold (%) =

$$\frac{(\text{Test group average post-value}) - (\text{Control group average post-value})}{(\text{Control group average pre-value}) - (\text{Control group average post-value})} \times 100$$

Table 7 shows the results (the highest recovery rates).

TABLE 7

| Ex. No. | Recovery rate (%) | Time to measure | Ex. No. | Recovery rate (%) | Time to measure |
|---|---|---|---|---|---|
| 1 | 72.3 | 60 min. later | 23 | 52.9 | 30 min. later |
| 2 | 40.2 | 60 min. later | 24 | 41.3 | 60 min. later |
| 3 | 33.3 | 30 min. later | 25 | 46.0 | 15 min. later |
| 5 | 51.9 | 30 min. later | 26 | 55.8 | 60 min. later |
| 7 | 52.3 | 60 min. later | 29 | 56.2 | 30 min. later |
| 8 | 83.9 | 60 min. later | 32 | 86.6 | 60 min. later |
| 9 | 56.2 | 60 min. later | 33 | 90.1 | 30 min. later |
| 11 | 48.8 | 60 min. later | 34 | 58.2 | 60 min. later |
| 12 | 58.8 | 60 min. later | 35 | 102.5 | 60 min. later |
| 13 | 32.7 | 15 min. later | 38 | 67.2 | 15 min. later |
| 14 | 69.5 | 15 min. later | 41* | 67.4 | 30 min. later |
| 16 | 35.1 | 30 min. later | 42 | 51.8 | 66 min. later |
| 17 | 95.9 | 60 min. later | 44 | 44.1 | 30 min. later |
| 19 | 91.7 | 60 min. later | 45 | 54.8 | 15 min. later |
| 20 | 33.8 | 30 min. later | 46 | 109.0 | 30 min. later |
| 21 | 81.3 | 60 min. later | 48 | 80.4 | 60 min. later |
| 22 | 54.4 | 60 min. later | 50 | 53.0 | 30 min. later |
| 52 | 65.1 | 30 min. later | 113 | 44.4 | 15 min. later |
| 53 | 58.7 | 30 min. later | 115 | 55.6 | 30 min. later |
| 65 | 32.0 | 30 min. later | 117 | 37.2 | 30 min. later |
| 80 | 30.4 | 15 min. later | 118 | 33.5 | 30 min. later |
| 81 | 31.2 | 15 min. later | 119 | 38.1 | 15 min. later |
| 88 | 59.5 | 60 min. later | 120 | 71.4 | 60 min. later |
| 89 | 33.3 | 15 min. later | 121 | 73.3 | 60 min. later |
| 90 | 53.1 | 30 min. later | 122 | 30.6 | 60 min. later |
| 91 | 53.1 | 30 min. later | 123 | 32.5 | 30 min. later |
| 95 | 38.4 | 15 min. later | 124 | 53.8 | 15 min. later |
| 96 | 102.0 | 60 min. later | 125 | 33.7 | 30 min. later |
| 103 | 35.0 | 30 min. later | 129 | 39.7 | 60 min. later |
| 104 | 63.5 | 60 min. later | 133 | 36.4 | 60 min. later |
| 111 | 62.1 | 30 min. later | 134 | 100.7 | 60 min. later |
| 112 | 37.9 | 15 min. later | | | |

*: dosage = 10 mg/kg

As shown in Tables 6 and 7, the compounds of the invention produce excellent analgesic effects.

FORMULATION EXAMPLE 1

Manufacture of Tablets

Using the compound of the invention obtained in Example 1 as an active ingredient, tablets (2000 tables) each containing 300 mg of the active ingredient were manufactured according to the following formula:

| | |
|---|---|
| Compound of Example 1 | 600 g |
| Lactose (product of Japanese pharmacopoeia: JP) | 67 g |
| Corn starch (JP) | 33 g |
| Calcium carboxymethyl cellulose (JP) | 25 g |
| Methyl cellulose (JP) | 12 g |
| Magnesium stearate (JP) | 3 g |

More specifically, the compound of Example 1, lactose, corn starch and calcium carboxymethyl cellulose according to the above formula were fully blended and granulated using an aqueous solution of methyl cellulose. The granulated mixture was passed through a 24-mesh sieve and the granules under the sieve were mixed with magnesium stearate and compression-molded into tablets to provide the object tablets.

FORMULATION EXAMPLE 2

Manufacture of Capsules

Using the compound of the invention obtained in Example 32 as an active ingredient, hard gelatin capsules (2000 units) each containing 200 mg of the active ingredient were manufactured according to the following formula:

| Compound of Example 32 | 400 g |
|---|---|
| Crystalline cellulose (JP) | 60 g |
| Corn starch (JP) | 34 g |
| Talc (JP) | 4 g |
| Magnesium stearate (JP) | 2 g |

More specifically, the ingredients according to the above formula were finely pulverized and blended to give a homogeneous composition. This composition was filled into proper-sized gelatin capsule shells for oral administration to provide the object capsules.

INDUSTRIAL APPLICABILITY

The pyrazolo[1,5-a]pyrimidine derivatives according to the present invention have potent analgesic effects and are useful as analgesics.

What is claimed is:

1. A pyrazolo[1,5-a]pyrimidine derivative of the following formula (1):

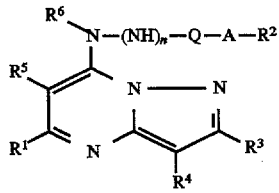

wherein $R^1$ is hydrogen, lower alkyl which may have thienyl, lower alkoxy, lower alkylthio, oxo or hydroxyl as a substituent, cycloalkyl, thienyl, furyl, lower alkenyl, or $R^1$ phenyl, said $R^1$ phenyl having 1 to 3 substituents selected from the group consisting of lower alkyl, lower alkoxy, phenylthio and halogen; $R^2$ is naphthyl, cycloalkyl, furyl, thienyl, pyridyl, halogen-substituted pyridyl, phenoxy, halogen-substituted phenoxy, or phenyl which may have 1 to 3 substituents selected from the group consisting of lower alkyl, lower alkoxy, halogen, nitro, halogen-substituted lower alkyl, halogen-substituted lower alkoxy, lower alkoxycarbonyl, hydroxyl, phenyl(lower)alkoxy, amino, cyano, lower alkanoyloxy, phenyl and di(lower) alkoxyphosphoryl(lower)alkyl; $R^3$ is hydrogen, phenyl or lower alkyl; $R^4$ is hydrogen, lower alkyl, lower alkoxycarbonyl, phenyl(lower)alkyl, phenyl, phenylthio-substituted phenyl, or halogen; $R^5$ is hydrogen or lower alkyl; $R^6$ is hydrogen, lower alkyl, phenyl(lower)alkyl, or an $R^6$ benzoyl, said $R^6$ benzoyl having 1 to 3 substituents selected from the group consisting of lower alkoxy, halogen-substituted lower alkyl and halogen; $R^1$ and $R^5$ may conjointly form lower alkylene; Q is carbonyl or sulfonyl; A is a single bond, lower alkylene or lower alkenylene; and n is 0 or 1.

2. A pyrazolo[1,5-a]pyrimidine derivative according to claim 1 which is selected from the group consisting of compounds of formula (1) wherein Q is carbonyl and n is 0, compounds wherein Q is carbonyl, n is 1, $R^1$ is lower alkyl or phenyl, $R^2$ is phenyl having 1 to 3 substituents selected from the group consisting of lower alkoxy and halogen-substituted lower alkyl, $R^3$, $R^4$, $R^5$ and $R^6$ are each hydrogen, and A is a single bond; and compounds wherein Q is sulfonyl, n is 0, $R^1$ is lower alkyl, $R^2$ is phenyl which may have 1 to 3 halogens, $R^3$, $R^4$, $R^5$ and $R^6$ are each hydrogen, and A is a single bond.

3. A pyrazolo[1,5-a]pyrimidine derivative according to claim 2 wherein $R^1$ is optionally lower alkylthio-substituted lower alkyl or optionally phenylthio-substituted phenyl, $R^2$ is phenyl having 1 to 3 substituents selected from the group consisting of lower alkoxy, halogen and halogen-substituted lower alkyl, $R^3$ is hydrogen or phenyl, $R^4$ is hydrogen, halogen or phenyl; $R^5$ is hydrogen; $R^6$ is hydrogen or benzoyl having halogen-substituted lower alkyl as a substituent, Q is carbonyl and A is a single bond.

4. A pyrazolo[1,5-a]pyrimidine derivative according to claim 3 wherein $R^3$, $R^4$ and $R^6$ are each hydrogen, n is 0, $R^1$ is n-butyl and $R^2$ is phenyl having either 2 to 3 lower alkoxy groups or 1 to 2 halogen-substituted lower alkyl groups, or $R^1$ is phenyl and $R^2$ is phenyl having 3 lower alkoxy groups.

5. A pyrazolo[1,5-a]pyrimidine derivative according to claim 4 wherein $R^2$ is 2,4-dimethoxyphenyl, 3,4,5-trimethoxyphenyl, 2-trifluoromethylphenyl or 2,5-bis(trifluoromethyl)phenyl.

6. A pyrazolo[1,5-a]pyrimidine derivative according to claim 5 which is selected from 5-n-butyl-7-(3,4,5-trimethoxybenzoylamino)pyrazolo[1,5-a]pyrimidine and 5-n-butyl-7-(2-trifluoromethylbenzoyl-amino) pyrazolo[1,5-a]pyrimidine.

7. A pyrazolo[1,5-a]pyrimidine derivative according to claim 6 which is 5-n-butyl-7-(3,4,5-trimethoxybenzoylamino)pyrazolo[1,5-a]pyrimidine.

8. An analgesic composition which comprises an effective amount of a pyrazolo[1,5-a]pyrimidine derivative defined in one of claims, 2–7 and 1 and a pharmaceutically acceptable carrier.

9. An analgesic composition which comprises an effective amount of 5-n-butyl-7-(3,4,5-trimethoxybenzoylamino)-pyrazolo[1,5-a]pyrimidine as an active ingredient and a pharmaceutically acceptable carrier.

10. A method for relieving pain, which comprises administering to a patient an effective amount of the pyrazolo[1,5-a]pyrimidine derivative defined in claim 1.

* * * * *